United States Patent
Kaasgaard et al.

(10) Patent No.: US 10,752,889 B2
(45) Date of Patent: *Aug. 25, 2020

(54) ALPHA-AMYLASE VARIANTS

(71) Applicant: NOVOZYMES A/S, Bagsvaerd (DK)

(72) Inventors: Svend Kaasgaard, Skovlunde (DK); Jens Oebro, Humlebaek (DK); Signe Eskildsen Larsen, Kgs. Lyngby (DK); Allan Svendsen, Hoersholm (DK); Annette Helle Johansen, Broenshoej (DK); Michael Skjoet, Jyllinge (DK); Carsten Andersen, Vaerloese (DK); Lars Beier, Soeborg (DK); Esben Peter Friis, Herlev (DK); Miguel Duarte Guilherme Pereira Toscano, Frederiksberg (DK); Mads Bjoernvad, Virum (DK); Frank Winther Rasmussen, Roskilde (DK); Liv Spaanger Christiansen, Gentofte (DK)

(73) Assignee: NOVOZYMES A/S, Bagsvaerd (DK)

( * ) Notice: Subject to any disclaimer, the term of this patent is extended or adjusted under 35 U.S.C. 154(b) by 90 days.

This patent is subject to a terminal disclaimer.

(21) Appl. No.: 16/190,580

(22) Filed: Nov. 14, 2018

(65) Prior Publication Data

US 2020/0172887 A1 Jun. 4, 2020

Related U.S. Application Data

(62) Division of application No. 15/218,599, filed on Jul. 25, 2016, now Pat. No. 10,167,458, which is a division of application No. 14/129,565, filed as application No. PCT/EP2012/062748 on Jun. 29, 2012, now Pat. No. 9,434,932.

(60) Provisional application No. 61/503,768, filed on Jul. 1, 2011.

(30) Foreign Application Priority Data

Jun. 30, 2011 (EP) .................................... 11172251

(51) Int. Cl.
*C12N 9/26* (2006.01)
*C12N 15/63* (2006.01)

(52) U.S. Cl.
CPC ........... *C12N 9/2414* (2013.01); *C12N 15/63* (2013.01); *C12Y 302/01001* (2013.01)

(58) Field of Classification Search
None
See application file for complete search history.

(56) References Cited

U.S. PATENT DOCUMENTS

| | | |
|---|---|---|
| 3,912,590 A | 10/1975 | Slott |
| 4,105,827 A | 8/1978 | Brichard |
| 4,106,991 A | 8/1978 | Markussen |
| 4,316,956 A | 2/1982 | Lutzen |
| 4,335,208 A | 6/1982 | Norman |
| 4,435,307 A | 3/1984 | Barbesgaard |
| 4,519,934 A | 5/1985 | Eilertsen |
| 4,643,736 A | 2/1987 | Cholley |
| 4,661,452 A | 4/1987 | Markussen |
| 4,683,202 A | 7/1987 | Mullis |
| 4,689,297 A | 8/1987 | Good |
| 5,227,084 A | 7/1993 | Martens |
| 5,231,017 A | 7/1993 | Lantero |
| 5,324,649 A | 6/1994 | Arnold |
| 5,336,611 A | 8/1994 | Van Eckelen |
| 5,453,216 A | 9/1995 | Kellett |
| 5,648,263 A | 7/1997 | Schulein |
| 5,691,178 A | 11/1997 | Schulein |
| 5,698,504 A | 12/1997 | Christie |
| 5,753,460 A | 5/1998 | Bisgaard-Frantzen |
| 5,766,371 A | 6/1998 | Bunch |
| 5,776,757 A | 7/1998 | Schulein |
| 5,814,501 A | 9/1998 | Becker |
| 5,856,164 A | 1/1999 | Outtrup |
| 5,888,954 A | 3/1999 | Haerer |
| 5,989,169 A | 11/1999 | Svendsen |
| 6,022,724 A | 2/2000 | Svendsen |
| 6,093,562 A | 7/2000 | Bisgaard-Frantzen |
| 6,143,708 A | 11/2000 | Svendsen |
| 6,187,576 B1 | 2/2001 | Svendsen |
| 6,211,134 B1 | 2/2001 | Caldwell |
| 6,287,841 B1 | 9/2001 | Mulleners |
| 6,297,037 B1 | 10/2001 | Barnett |
| 6,297,038 B1 | 10/2001 | Bisgaard-Frantzen |
| 6,361,989 B1 | 2/2002 | Svendsen |
| 6,410,295 B1 | 6/2002 | Andersen |

(Continued)

FOREIGN PATENT DOCUMENTS

DE 102004020082 A1 5/2005
DE 102006022216 A1 11/2007

(Continued)

OTHER PUBLICATIONS

Maurer, 2004, Curr Opin Biotechnol 15, 330-334.
Gruden, 1994, Eur. J. Biochem. 224, 507-518—See Control No. 90/012,512.
Remerowski, 1996, Eur. J. Biochem. 235, 629-640.

(Continued)

*Primary Examiner* — Suzanne M Noakes
*Assistant Examiner* — Jae W Lee
(74) *Attorney, Agent, or Firm* — David Fazzolare

(57) ABSTRACT

The present invention relates to variants of a parent alpha-amylase. The present invention also relates to polynucleotides encoding the variants; nucleic acid constructs, vectors, and host cells comprising the polynucleotides; and methods of using the variants.

21 Claims, No Drawings
Specification includes a Sequence Listing.

(56) References Cited

U.S. PATENT DOCUMENTS

| | | |
|---|---|---|
| 6,440,716 B1 | 8/2002 | Svendsen |
| 6,475,762 B1 | 11/2002 | Stafford |
| 6,528,298 B1 | 3/2003 | Svendsen |
| 6,562,612 B2 | 5/2003 | Jones |
| 6,623,948 B1 | 9/2003 | Outtrup |
| 6,670,314 B2 | 12/2003 | Smith |
| 6,743,616 B2 | 6/2004 | Araki |
| 6,867,031 B2 | 3/2005 | Bisgaard-Frantzen |
| 6,995,125 B2 | 2/2006 | Dasque |
| 6,998,375 B2 | 2/2006 | Kapur |
| 7,115,409 B1 | 10/2006 | Svendsen |
| 7,153,818 B2 | 12/2006 | Breves |
| 7,163,816 B2 | 1/2007 | Svendsen |
| 7,378,264 B2 | 5/2008 | Svendsen |
| 7,432,099 B2 | 10/2008 | Andersen |
| 7,498,158 B2 | 3/2009 | Svendsen |
| 7,521,411 B2 | 4/2009 | Sharma |
| 7,541,026 B2 | 6/2009 | Power |
| 7,579,310 B2 | 8/2009 | Kasturi |
| 7,713,723 B1 | 5/2010 | Thisted |
| 7,727,946 B2 | 6/2010 | Catalfamo |
| 7,993,897 B2 | 8/2011 | Svendsen |
| 8,008,241 B2 | 8/2011 | Souter |
| 8,071,345 B2 | 12/2011 | Nielsen |
| 8,080,401 B2 * | 12/2011 | Bessler .............. C11D 3/38681 435/202 |
| 8,680,034 B2 | 3/2014 | Souter |
| 8,883,970 B2 | 11/2014 | Andersen |
| 2001/0039253 A1 | 11/2001 | Borchert |
| 2001/0329253 | 11/2001 | Borchert |
| 2002/0082186 A1 | 6/2002 | Smith |
| 2002/0137648 A1 | 9/2002 | Sharma |
| 2002/0155574 A1 | 10/2002 | Thisted |
| 2002/0198125 A1 | 12/2002 | Jones |
| 2003/0171235 A1 | 9/2003 | Hansen |
| 2003/0171236 A1 | 9/2003 | Svendsen |
| 2004/0096952 A1 | 5/2004 | Svendsen |
| 2004/0138078 A1 | 7/2004 | Clare |
| 2004/0147008 A1 | 7/2004 | Draborg |
| 2004/0259749 A1 | 12/2004 | Braeckman |
| 2005/0061703 A1 | 3/2005 | Catlin |
| 2005/0084937 A1 | 4/2005 | Borchert |
| 2005/0170487 A1 | 8/2005 | Svendsen |
| 2006/0035323 A2 | 2/2006 | Bisgard |
| 2006/0090779 A1 | 5/2006 | Sharma |
| 2006/0097424 A1 | 5/2006 | Sharma |
| 2006/0205628 A1 | 7/2006 | Deinhammer |
| 2006/0257596 A1 | 11/2006 | Catalfamo |
| 2007/0004612 A1 | 1/2007 | Caitlin |
| 2007/0012815 A1 | 1/2007 | Kroll |
| 2007/0190632 A1 | 8/2007 | Bessler |
| 2007/0191248 A1 | 8/2007 | Souter |
| 2007/0212768 A1 | 9/2007 | Bessler |
| 2008/0004201 A1 | 1/2008 | Boutique |
| 2008/0014392 A1 | 1/2008 | Ayats |
| 2008/0063774 A1 | 3/2008 | Aehle |
| 2008/0193999 A1 | 8/2008 | Andersen |
| 2008/0209863 A1 | 9/2008 | Catlin |
| 2008/0220498 A1 | 9/2008 | Cervin |
| 2009/0082246 A1 | 3/2009 | Andersen |
| 2009/0117642 A1 | 5/2009 | Power |
| 2009/0143270 A1 | 6/2009 | Svendsen |
| 2009/0233830 A1 | 9/2009 | Dirr |
| 2009/0233832 A1 | 9/2009 | Souter |
| 2009/0314286 A1 | 12/2009 | Cuevas |
| 2010/0144575 A1 | 6/2010 | Svendsen |
| 2011/0195481 A1 | 8/2011 | Svendsen |
| 2011/0212876 A1 | 9/2011 | Meek |
| 2011/0275136 A1 | 11/2011 | Andersen |
| 2012/0045817 A1 | 2/2012 | Estell |
| 2012/0045822 A1 | 2/2012 | Concar |
| 2012/0015673 A1 | 6/2012 | Cuevas |
| 2013/0000055 A1 | 1/2013 | Jackson |

FOREIGN PATENT DOCUMENTS

| | | |
|---|---|---|
| DE | 102006022224 A1 | 11/2007 |
| EP | 0063909 A1 | 11/1982 |
| EP | 0119920 A2 | 9/1984 |
| EP | 0218272 A1 | 4/1987 |
| EP | 0252666 A2 | 1/1988 |
| EP | 0252730 A2 | 1/1988 |
| EP | 0258068 A2 | 3/1988 |
| EP | 0260105 A2 | 3/1988 |
| EP | 00305216 A1 | 3/1989 |
| EP | 0407225 A1 | 1/1991 |
| EP | 1199356 A2 | 4/2002 |
| EP | 1707624 A2 | 4/2006 |
| EP | 1022334 B1 | 8/2007 |
| EP | 2308980 A2 | 4/2011 |
| GB | 1296839 | 11/1972 |
| GB | 1372034 | 10/1974 |
| GB | 1466799 A | 3/1977 |
| JP | 64-074992 | 3/1989 |
| WO | 89/06270 A1 | 7/1989 |
| WO | 89/06279 A1 | 7/1989 |
| WO | 89/09259 A1 | 10/1989 |
| WO | 90/011352 A1 | 10/1990 |
| WO | 90/012876 A1 | 11/1990 |
| WO | 91/00353 A2 | 1/1991 |
| WO | 91/16422 A1 | 10/1991 |
| WO | 91/17243 A1 | 11/1991 |
| WO | 92/06165 A1 | 4/1992 |
| WO | 92/06221 A1 | 4/1992 |
| WO | 92/017601 A1 | 10/1992 |
| WO | 92/05249 A1 | 11/1992 |
| WO | 92/19708 A1 | 11/1992 |
| WO | 92/19709 A1 | 11/1992 |
| WO | 92/19729 A1 | 11/1992 |
| WO | 93/009244 A1 | 5/1993 |
| WO | 93/24618 A1 | 12/1993 |
| WO | 94/01541 A1 | 1/1994 |
| WO | 94/02597 A1 | 2/1994 |
| WO | 94/18314 A1 | 8/1994 |
| WO | 94/22800 A1 | 10/1994 |
| WO | 94/23053 A1 | 10/1994 |
| WO | 94/25578 A1 | 11/1994 |
| WO | 94/25583 A1 | 11/1994 |
| WO | 94/26859 A1 | 11/1994 |
| WO | 94/26860 A1 | 11/1994 |
| WO | 95/06720 A1 | 3/1995 |
| WO | 95/10591 A1 | 4/1995 |
| WO | 95/10602 A1 | 4/1995 |
| WO | 95/10603 A1 | 4/1995 |
| WO | 95/14807 A1 | 6/1995 |
| WO | 95/21247 A1 | 8/1995 |
| WO | 95/22615 A1 | 8/1995 |
| WO | 95/22625 A1 | 8/1995 |
| WO | 95/26397 A1 | 10/1995 |
| WO | 95/26397 A2 | 10/1995 |
| WO | 95/29982 A1 | 11/1995 |
| WO | 95/30744 A2 | 11/1995 |
| WO | 95/35381 A1 | 12/1995 |
| WO | 95/35382 A2 | 12/1995 |
| WO | 96/00292 A1 | 1/1996 |
| WO | 96/01323 A1 | 1/1996 |
| WO | 96/002633 A1 | 2/1996 |
| WO | 96/05295 A1 | 2/1996 |
| WO | 96/12012 A1 | 4/1996 |
| WO | 96/13580 A1 | 5/1996 |
| WO | 96/23873 A1 | 8/1996 |
| WO | 96/23874 A2 | 8/1996 |
| WO | 96/27002 A1 | 9/1996 |
| WO | 96/28567 A1 | 9/1996 |
| WO | 96/30481 A1 | 10/1996 |
| WO | 96/38578 A1 | 12/1996 |
| WO | 96/39528 A2 | 12/1996 |
| WO | 97/00324 A1 | 1/1997 |
| WO | 97/04079 A1 | 2/1997 |
| WO | 97/07202 A1 | 2/1997 |
| WO | 97/41213 A2 | 11/1997 |
| WO | 97/43424 A1 | 11/1997 |
| WO | 98/05748 A1 | 2/1998 |

(56) References Cited

FOREIGN PATENT DOCUMENTS

| | | | |
|---|---|---|---|
| WO | 98/15257 A1 | 4/1998 | |
| WO | 98/20115 A1 | 5/1998 | |
| WO | 98/20116 A1 | 5/1998 | |
| WO | 98/23732 A2 | 6/1998 | |
| WO | 98/34946 A1 | 8/1998 | |
| WO | 99/06521 A1 | 2/1999 | |
| WO | 99/09183 A2 | 2/1999 | |
| WO | 99/19467 A1 | 4/1999 | |
| WO | 99/19467 A2 | 4/1999 | |
| WO | 99/20770 A2 | 4/1999 | |
| WO | 99/023211 A1 | 5/1999 | |
| WO | 99/23211 A1 | 5/1999 | |
| WO | 99/28448 A1 | 6/1999 | |
| WO | 99/29876 A2 | 6/1999 | |
| WO | 99/042567 A1 | 8/1999 | |
| WO | 99/49740 A1 | 10/1999 | |
| WO | 00/04136 A1 | 1/2000 | |
| WO | 00/29560 A2 | 5/2000 | |
| WO | 00/60058 A2 | 10/2000 | |
| WO | 00/60059 A2 | 10/2000 | |
| WO | 00/60060 A2 | 10/2000 | |
| WO | 00/060060 A2 | 10/2000 | |
| WO | 01/04273 A2 | 1/2001 | |
| WO | 01/014532 A2 | 3/2001 | |
| WO | 01/064852 A1 | 9/2001 | |
| WO | 01/66712 A2 | 9/2001 | |
| WO | 02/06438 A1 | 1/2002 | |
| WO | 02/08380 A1 | 1/2002 | |
| WO | 02/10355 A2 | 2/2002 | |
| WO | 02/14490 A2 | 2/2002 | |
| WO | 02/31124 A2 | 4/2002 | |
| WO | 02/092797 A2 | 11/2002 | |
| WO | 02/102955 A1 | 12/2002 | |
| WO | 04/111178 A1 | 12/2004 | |
| WO | 05/052146 A2 | 6/2005 | |
| WO | 05/052161 A2 | 6/2005 | |
| WO | 2005/121302 A1 | 12/2005 | |
| WO | 06/002643 A2 | 1/2006 | |
| WO | 2006/002643 A2 | 1/2006 | |
| WO | 06/043178 A2 | 4/2006 | |
| WO | 06/060062 A2 | 6/2006 | |
| WO | 07/044993 A2 | 4/2007 | |
| WO | 2007/087318 A2 | 8/2007 | |
| WO | 2007/087319 A2 | 8/2007 | |
| WO | 2007/131656 A1 | 11/2007 | |
| WO | 2007/131657 A2 | 11/2007 | |
| WO | 2007/145964 A2 | 12/2007 | |
| WO | 08/02472 A2 | 1/2008 | |
| WO | 2008/010925 A2 | 1/2008 | |
| WO | 08/153925 A9 | 12/2008 | |
| WO | 2009/040544 A1 | 2/2009 | |
| WO | 09/61378 A2 | 5/2009 | |
| WO | 09/61379 A2 | 5/2009 | |
| WO | 09/61381 A2 | 5/2009 | |
| WO | 2009/102854 A1 | 8/2009 | |
| WO | 2013/001078 A1 | 1/2013 | |
| WO | 2013/001087 A1 | 1/2013 | |
| WO | 2013/003659 A1 | 1/2013 | |

OTHER PUBLICATIONS

Focus on Surfactants 2004, Elsevier 2004(12), 3.
U.S. Appl. No. 14/151,875 US Office Action dated Aug. 11, 2014.
Aehle, 2007 XP002489592; ISBN; 978-3-527-31689-2; p. 178-193—See Control No. 90/012,512.
Needleman 1970, J. Mol. Biol 48, 443-453.
Branden 1991, Introduction to Protein Structure, Garland Publishing Inc., New York p. 247—See Control No. 90/012,512.
Seffernick 2001, J. Bacteriol 183(8), 2405-2410.
Witkowski 1999, Biochemistry 38, 11643-11650.
Protease Novozymes Savinase, National Center for Biotechnology Education, University of Reading, http://www.ncbe.reading.ac.uk/ncbe/material/enzymes/savinase.html NCBE, 2011—See Control No. 90/012,512.
Focus on Surfactants Elsevier 2007(9), p. 5 XP022302950, ISSN:1351-4210—See Control No. 90/012,512.
File History from EP2100947 dated Jun. 6, 2013—See Control No. 90/012,512.
File History from EP2100949 dated Jun. 6, 2013—See Control No. 90/012,512.
All Office Actions, U.S. Appl. No. 13/189,610.
All Office Actions, U.S. Appl. No. 12/397,489.
All Office Actions, U.S. Appl. No. 12/397,515.
All Office Actions, U.S. Appl. No. 12/397,497.
Altschul, et al., "Gapped BLAST and PSI-BLAST: a new generation of protein database search programs", Nucleic Acids Res., vol. 25, pp. 3389-3402 (1997).
Beaucage et al., "Deoxynucleoside phosphoramidites—A new class of key intermediates for deoxypolynucleotide synthesis", Tetrahedron Lett., vol. 22, No. 20, pp. 1859-1862 (1981).
Boel et al., "Glucoamylases G1 and G2 from Aspergillus niger are synthesized from two different but closely related mRNAs", The EMBO Journal, vol. 3, No. 5, pp. 1097-1102 (1984).
Cha et al., "Lowering the pH optimum of D-xylose isomerase: the effect of mutations of the negatively charged residues", Molecules and Cells, vol. 8, No. 4, pp. 374-382 (1998).
Cohen et al., "In vitro enzyme evolution: the screening challenge of isolating the one in a million", Trends in Biotechnology, vol. 19, No. 12, pp. 507-510 (2001).
Hahn et al., "Regulatory inputs for the synthesis of ComK, the competence transcription factor of Bacillus subtilis", Molecular Microbiology, vol. 21, No. 4, pp. 763-775 (1996).
Huber et al., "Protein fold recognition without Boltzmann statistics or explicit physical basis", Protein Science, vol. 7, No. 1, pp. 142-149 (1998).
Dartois et al., "Cloning, nucleotide sequence and expression in Escherichia coli of a lipase gene from Bacillus subtilis", Biochimica et Biophysica Acta, vol. 1131, No. 3, pp. 253-260 (1992).
Engelen et al., "Simple and rapid determination of phytase activity", Journal of AOAC International, vol. 77, No. 3, pp. 760-764 (1994).
Freire, "Differential Scanning Calorimetry", In Protein Stability and Folding: Theory and Practice, Methods in Molecular Biology, No. 40, ed. B.A. Shirley, New York: Humana Press pp. 191-218 (1995).
Gaboriaud et al., "Hydrophobic cluster analysis: an efficient new way to compare and analyse amino acid sequences", FEBS Letters, vol. 224, No. 1, pp. 149-155 (1987).
Holm et al., "Random mutagenesis used to probe the structure and function of Bacillus stearothermophilus alpha-amylase", Protein Engineering, vol. 3, No. 3, pp. 181-191 (1990).
Matthes et al., "Simulataneous rapid chemical synthesis of over one hundred oligonucleotides on a microscale", EMBO Journal, vol. 3, No. 4, pp. 801-805 (1984).
McKenzie et al., "The nucleotide sequence of pUB110: some salient features in relation to replication and its regulation", Plasmid, vol. 15, No. 2, pp. 93-103 (1986).
Needleman et al., "A general method applicable to the search for similarities in the amino acid sequence of two proteins", Journal Mol. Biol, vol. 48, No. 3, pp. 443-453 (1970).
Niedhardt et al., "Culture medium for Enterobacteria", J. Bacteriology, vol. 119, No. 3, pp. 736-747 (1974).
Pearson et al., "Improved tools for biological sequence comparison", Proc. Natl. Acad. Sci USA, vol. 85, No. 8, pp. 2444-2448 (1988).
Vogtentanz et al., "A Bacillus subtilis fusion protein system to produce soybean Bowman-Birk protease inhibitor", Protein Expression and Purification, vol. 55, No. 1, pp. 40-52 (2007).
Russell et al., "Electrostatic effects on modification of charged groups in the active site cleft of subtilis by protein engineering", Journal of Molecular Biology, vol. 193, No. 4, pp. 803-813 (1987).
Sambrook et al, Molecular Cloning: A Laboratory Manual, 2nd ed. New York; Cold Spring Harbor Press, (1989).
Smirnova et al., "Mutation in x-amylase gene of Bacillus amyloliquefaciens leading to reduction in temperature of protein inactivation", Molecular Biology Journal, vol. 22, No. 5, pp. 921-1036 (1988).
Tsukamoto et al., "Nucleotide sequence of the maltohexaose-producing amylase gene from an alkalophilic Bacillus sp. #707 and

(56) References Cited

OTHER PUBLICATIONS structural similarity to liquefying type alpha-amylases", Biochemical and Biophysical Research Communications, vol. 151, No. 1, pp. 25-31 (1988).

Novozymes A/S v Genencor International Inc. and Enzyme Development Corporation, 446 F.Supp.2d 297 (Aug. 24, 1996).

Novozymes A/S v Genencor International Inc. and Enzyme Development Corporation, 474 F.Supp.2d 592 (Feb. 16, 1997).

Branden et al., "Prediction, Engineering, and Design of Protein Structures", Introduction to Protein Structure, p. 247 (1991).

Declerk et al., "Probing Structural Determinants Specifying High", J. Mol. Biol., vol. 301, pp. 1041-1057 (2000).

Guo et al., "Protein Tolerance to Random Amino Acid Change", PNAS, vol. 101, No. 25 pp. 9205-9210 (2004).

Jorgensen et al., PIR Accession No. A54541 (1995).

Seffernick, "Melamine Deaminase and Atrazine Chlorohydrolase: 98 Percent Identical But Functionally Different", Journal of Bacteriology, vol. 183, No. 8, pp. 2405-2410 (2001).

Takkinen et al. PIR Accession No. A92389 (1983).

Witkowski et al., "Conversion of a B-Ketoacyl Synthase to a Malonyl", Biochemistry, vol. 38, pp. 11643-11650 (1999).

Gray, 166 J Bacteriology 635, 1986.

Declerck et al, 2002, Biologia 57(11), 203-211.

Igarashi et al, 1998, Biochem Biophys Res Com 248(2), 372-377.

Shiau 2003, Appl Environ Micro 69(4), 2383-2385.

Suzuki et al, 1989, J Biol Chem 264(32), 18933-18938.

*Danisco v. Novozymes A/S and Novozymes North America, Inc.*, USDC, Northern District of California, Civil Action No. CV124502—Aug. 27, 2012.

*Danisco v. Novozymes A/S and Novozymes North America, Inc.*, USDC, Northern District of Iowa, Case No. 1:12-CV-00085-EJM—Aug. 27, 2012

*Danisco v. Novozymes A/S and Novozymes North America, Inc.*, USDC, Northern District of California, Order Granting Motion to Dismiss No. CV124502 RS—Jan. 7, 2013.

Declerk, N. et al. 2002, Biologia Bratislava vol. 57, Supp 11, pp. 203-211.

Kanan, R. at al. 2005, Protein Science 15(3), 468-477.

Davies, G.J. et al. 2004, Acta Crystallographica D. 61, 190-193

Lange, G. et al. 1994, Eur. J. Biochem. 224, 507-518.

\* cited by examiner

ALPHA-AMYLASE VARIANTS

CROSS-REFERENCE TO RELATED APPLICATIONS

This application is a division of U.S. application Ser. No. 15/218,599 filed Jul. 25, 2016, now allowed, which is a division of U.S. application Ser. No. 14/129,565 filed Feb. 4, 2014, now U.S. Pat. No. 9,434,932, which is a 35 U.S.C. 371 national application of PCT/EP2012/062748 filed Jun. 29, 2012, which claims priority or the benefit under 35 U.S.C. 119 of European application no. 11172251.8 filed Jun. 30, 2011 and U.S. provisional application No. 61/503,768 filed Jul. 1, 2011, the contents of which are fully incorporated herein by reference.

REFERENCE TO A JOINT RESEARCH AGREEMENT

The inventions claimed in the present application were made under a joint research agreement between The Procter & Gamble Company and Novozymes A/S.

REFERENCE TO A SEQUENCE LISTING

This application contains a Sequence Listing in computer readable form, which is incorporated herein by reference.

BACKGROUND OF THE INVENTION

Field of the Invention

The present invention relates to variants of an alpha-amylase, polynucleotides encoding the variants, methods of producing the variants, and methods of using the variants.

Description of the Related Art

Alpha-amylases (alpha-1,4-glucan-4-glucanohydrolases, E.C. 3.2.1.1) constitute a group of enzymes, which catalyses hydrolysis of starch and other linear and branched 1,4-gluosidic oligo- and polysaccharides.

There is a long history of industrial use of alpha-amylases in several known applications such as detergent, baking, brewing, starch liquefaction and saccharification e.g. in preparation of high fructose syrups or as part of ethanol production from starch. These and other applications of alpha-amylases are known and utilize alpha-amylases derived from microorganisms, in particular bacterial alpha-amylases.

Among the first bacterial alpha-amylases to be used were an alpha-amylase from *B. licheniformis*, also known as Termamyl which have been extensively characterized and the crystal structure has been determined for this enzyme. Alkaline amylases, such as AA560, form a particular group of alpha-amylases that have found use in detergents. Many of these known bacterial amylases have been modified in order to improve their functionality in a particular application.

Methods of increasing the thermostability of alpha-amylases have been well studied. Suzuki et al. (1989) disclose chimeric alpha-amylases, in which specified regions of a *B. amyloliquefaciens* alpha-amylase have been substituted for the corresponding regions of a *B. licheniformis* alpha-amylase. The chimeric alpha-amylases were constructed with the purpose of identifying regions responsible for thermostability. Such regions were found to include amino acid residues 177-186 and amino acid residues 255-270 of the *B. amyloliquefaciens* alpha-amylase. Igarashi et al. 1998 show that the thermostability of AmyS-type amylases can be increased by the deletion of two amino acid residues, R179-G180, (AmyS numbering) from a loop (F 178 to A184). However, Shiau et al. (2003) showed that an AmyS enzyme with deletion in the same loop has a lower specific activity for corn starch hydrolysis at high-temperature than the parent enzyme, negating one of the principal advantages of AmyS amylases.

For environmental reasons it has been increasingly important to lower the temperature in washing, dishwashing and/or cleaning processes. However, most enzymes including amylases have a temperature optimum which is above the temperature usually used in low temperature washing. Alpha-amylase is a key enzyme for use in detergent compositions and its use has become increasingly important for removal of starchy stains during laundry washing or dishwashing. Therefore, it is important to find alpha-amylase variants, which retain their wash performance, stain removal effect and/or activity when the temperature is lowered. However, despite the efficiency of current detergents enzyme compositions, there are many stains that are difficult to completely remove. These problems are compounded by the increased use of low (e.g., cold water) wash temperatures and shorter washing cycles. Thus, it is desirable to have amylolytic enzymes that can function under low temperature and at the same time preserve or increase other desirable properties such as specific activity (amylolytic activity), stability and/or wash performance.

Thus, it is an object of the present invention to provide alpha-amylase variants which could be used in washing, dishwashing and/or cleaning processes at low temperature, such as temperatures of 5-35° C. It is a further object of the present invention to provide alpha-amylase variants which have improved wash performance at low temperature compared to the parent alpha-amylase or compared to the alpha-amylase of any of SEQ ID NO: 1, 2, 3, 4, 5, 6, 7, 8, 9, 10, 11 or 12.

SUMMARY OF THE INVENTION

The present invention relates to isolated variants of a parent alpha-amylase, comprising an alteration at two or more (several) positions corresponding to positions G304, W140, W189, D134, E260, F262, W284, W347, W439, W469, G476, and G477 of the mature polypeptide of SEQ ID NO: 1, wherein each alteration is independently a substitution, deletion or insertion, and wherein the variant has at least 80% but less than 100% sequence identity with the mature polypeptide of any of SEQ ID NOs 1, 2, 3, 4, 5, 6, 7, 8, 9, 10, 11 or 12, and wherein the variant has alpha-amylase activity.

The present invention also relates to isolated polynucleotides encoding the variants; nucleic acid constructs, vectors, and host cells comprising the polynucleotides; and methods of producing the variants.

The present invention also relates to methods for preparing such variants.

DETAILED DESCRIPTION OF THE INVENTION

The present invention relates to isolated variants of a parent alpha-amylase, comprising an alteration at two or more (several) positions corresponding to positions G304, W140, W189, D134, E260, F262, W284, W347, W439, W469, G476, and G477 of the mature polypeptide of SEQ ID NO: 1, wherein each alteration is independently a substitution, deletion or insertion, and wherein the variant has at least 80% but less than 100% sequence identity with the mature polypeptide of any of SEQ ID NOs 1, 2, 3, 4, 5, 6, 7, 8, 9, 10, 11 or 12, and wherein the variant has alpha-amylase activity Definitions Alpha-amylase activity: The term "alpha-amylase activity" means the activity of alpha-1,4-glucan-4-glucanohydrolases, E.C. 3.2.1.1, which constitute a group of enzymes, which catalyze hydrolysis of starch and other linear and branched 1,4-glucosidic oligo- and polysaccharides.

Variant: The term "variant" means a polypeptide having alpha-amylase activity comprising an alteration, i.e., a substitution, insertion, and/or deletion, at one or more (several) positions. A substitution means a replacement of an amino acid occupying a position with a different amino acid; a deletion means removal of an amino acid occupying a position; and an insertion means adding 1-3 amino acids adjacent to an amino acid occupying a position.

Mutant: The term "mutant" means a polynucleotide encoding a variant.

Wild-Type Enzyme: The term "wild-type" alpha-amylase means an alpha-amylase expressed by a naturally occurring microorganism, such as a bacterium, yeast, or filamentous fungus found in nature.

Parent or Parent alpha-amylase: The term "parent" or "parent alpha-amylase" means an alpha-amylase to which an alteration is made to produce the enzyme variants of the present invention. The parent may be a naturally occurring (wild-type) polypeptide or a variant thereof.

Isolated variant: The term "isolated variant" means a variant that is modified by the hand of man. In one aspect, the variant is at least 1% pure, e.g., at least 5% pure, at least 10% pure, at least 20% pure, at least 40% pure, at least 60% pure, at least 80% pure, and at least 90% pure, as determined by SDS-PAGE.

Substantially pure variant: The term "substantially pure variant" means a preparation that contains at most 10%, at most 8%, at most 6%, at most 5%, at most 4%, at most 3%, at most 2%, at most 1%, and at most 0.5% by weight of other polypeptide material with which it is natively or recombinantly associated. Preferably, the variant is at least 92% pure, e.g., at least 94% pure, at least 95% pure, at least 96% pure, at least 97% pure, at least 98% pure, at least 99% pure, at least 99.5% pure, and 100% pure by weight of the total polypeptide material present in the preparation. The variants of the present invention are preferably in a substantially pure form. This can be accomplished, for example, by preparing the variant by well known recombinant methods or by classical purification methods.

Mature polypeptide: The term "mature polypeptide" means a polypeptide in its final form following translation and any post-translational modifications, such as N-terminal processing, C-terminal truncation, glycosylation, phosphorylation, etc.

Mature polypeptide coding sequence: The term "mature polypeptide coding sequence" means a polynucleotide that encodes a mature polypeptide having alpha-amylase activity.

Sequence Identity: The relatedness between two amino acid sequences or between two nucleotide sequences is described by the parameter "sequence identity".

For purposes of the present invention, the degree of sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−
Total Number of Gaps in Alignment)

For purposes of the present invention, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of
Alignment−Total Number of Gaps in Alignment)

Fragment: The term "fragment" means a polypeptide having one or more (several) amino acids deleted from the amino and/or carboxyl terminus of a mature polypeptide; wherein the fragment has alpha-amylase activity.

Subsequence: The term "subsequence" means a polynucleotide having one or more (several) nucleotides deleted from the 5'- and/or 3'-end of a mature polypeptide coding sequence; wherein the subsequence encodes a fragment having alpha-amylase activity.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Isolated polynucleotide: The term "isolated polynucleotide" means a polynucleotide that is modified by the hand of man. In one aspect, the isolated polynucleotide is at least 1% pure, e.g., at least 5% pure, at least 10% pure, at least 20% pure, at least 40% pure, at least 60% pure, at least 80% pure, at least 90% pure, and at least 95% pure, as determined by agarose electrophoresis. The polynucleotides may be of genomic, cDNA, RNA, semisynthetic, synthetic origin, or any combinations thereof.

Substantially pure polynucleotide: The term "substantially pure polynucleotide" means a polynucleotide preparation free of other extraneous or unwanted nucleotides and in a form suitable for use within genetically engineered polypeptide production systems. Thus, a substantially pure polynucleotide contains at most 10%, at most 8%, at most 6%, at most 5%, at most 4%, at most 3%, at most 2%, at most 1%, and at most 0.5% by weight of other polynucleotide material with which it is natively or recombinantly associated. A substantially pure polynucleotide may, however, include naturally occurring 5'- and 3'-untranslated regions, such as promoters and terminators. It is preferred that the substantially pure polynucleotide is at least 90% pure, e.g., at least 92% pure, at least 94% pure, at least 95% pure, at least 96% pure, at least 97% pure, at least 98% pure, at least 99% pure, and at least 99.5% pure by weight. The polynucleotides of the present invention are preferably in a substantially pure form.

Coding sequence: The term "coding sequence" means a polynucleotide, which directly specifies the amino acid sequence of its polypeptide product. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant polynucleotide.

cDNA: The term "cDNA" means a DNA molecule that can be prepared by reverse transcription from a mature, spliced, mRNA molecule obtained from a eukaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present invention.

Control sequences: The term "control sequences" means all components necessary for the expression of a polynucleotide encoding a variant of the present invention. Each control sequence may be native or foreign to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

Operably linked: The term "operably linked" means a configuration in which a control sequence is placed at an appropriate position relative to the coding sequence of a polynucleotide such that the control sequence directs the expression of the coding sequence.

Expression: The term "expression" includes any step involved in the production of the variant including, but not limited to, transcription, post-transcriptional modification, translation, post-translational modification, and secretion.

Expression vector: The term "expression vector" means a linear or circular DNA molecule that comprises a polynucleotide encoding a variant and is operably linked to additional nucleotides that provide for its expression.

Host cell: The term "host cell" means any cell type that is susceptible to transformation, transfection, transduction, and the like with a nucleic acid construct or expression vector comprising a polynucleotide of the present invention. The term "host cell" encompasses any progeny of a parent cell that is not identical to the parent cell due to mutations that occur during replication.

Starch removing process: The expression "starch removing process" relates to any kind of process whereby starch is removed (or converted) such as in washing processes where starch is removed from textile e.g. textile cleaning such as laundry. A starch removing process could also be hard surface cleaning such as dish wash or it could be cleaning processes in general such as industrial or institutional cleaning. The expression also comprises other starch removing processes or starch conversion, ethanol production, starch liquefaction, textile desizing, paper and pulp production, beer making and detergents in general.

Improved property: The term "improved property" means a characteristic associated with a variant that is improved compared to the parent. Such improved properties include, but are not limited to, thermal activity, thermostability, pH activity, pH stability, substrate/cofactor specificity, improved surface properties, product specificity, increased stability or solubility in the presence of pretreated biomass, improved stability under storage conditions, and chemical stability.

Wash performance: In the present context the term "wash performance" is used as an enzyme's ability to remove starch or starch-containing stains present on the object to be cleaned during e.g. laundry or hard surface cleaning, such as dish wash. The wash performance may be quantified by calculating the so-called intensity value (Int) defined in the description of AMSA or in the beaker wash performance test in the Methods section below.

Improved wash performance: The term "improved wash performance" is defined herein as a variant enzyme displaying an alteration of the wash performance of an amylase variant relative to the wash performance of the parent amylase or relative to an alpha-amylase having the identical amino acid sequence of said variant but not having the deletion at one or more of the specified positions or relative to the activity of an alpha-amylase having the amino acid sequence shown in SEQ ID NO 4, e.g. by increased stain removal. The term "wash performance" includes cleaning in general e.g. hard surface cleaning as in dish wash, but also wash performance on textiles such as laundry, and also industrial and institutional cleaning.

Low temperature: "Low temperature" is a temperature of 5-35° C., preferably 5-30° C., more preferably 5-25° C., more preferably 5-20° C., most preferably 5-15° C., and in particular 5-10° C. In a preferred embodiment, "Low temperature" is a temperature of 10-35° C., preferably 10-30° C., more preferably 10-25° C., most preferably 10-20° C., and in particular 10-15° C.

Conventions for Designation of Variants

For purposes of the present invention, the mature polypeptide disclosed in SEQ ID NO: 1 is used to determine the corresponding amino acid residue in another alpha-amylase. The amino acid sequence of another alpha-amylase is aligned with the mature polypeptide disclosed in SEQ ID NO: 1, SEQ ID NO: 2, SEQ ID NO: 3, SEQ ID NO: 4, SEQ ID NO: 5, SEQ ID NO: 6, and based on the alignment, the amino acid position number corresponding to any amino acid residue in the mature polypeptide disclosed in SEQ ID NO: 1 is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0 or later.

Identification of the corresponding amino acid residue in another alpha-amylase can be confirmed by an alignment of multiple polypeptide sequences using "ClustalW" (Larkin et al., 2007, *Bioinformatics* 23: 2947-2948).

When the other enzyme has diverged from the mature polypeptide of SEQ ID NO: 1, SEQ ID NO: 2, SEQ ID NO: 3, SEQ ID NO: 4, SEQ ID NO: 5, or SEQ ID NO: 6 such that traditional sequence-based comparison fails to detect their relationship (Lindahl and Elofsson, 2000, *J. Mol. Biol.* 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the polypeptide has one or more representatives in the protein structure databases. Programs such as GenTHREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. Two or more protein structures can be aligned using a variety of algorithms such as the distance alignment matrix (Holm and Sander, 1998, *Proteins* 33: 88-96) or combinatorial extension (Shindyalov and Bourne, 1998, *Protein Engineering* 11: 739-747), and implementations of these algorithms can additionally be utilized to query structure databases with a structure of interest in order to discover possible structural homologs (e.g., Holm and Park, 2000, *Bioinformatics* 16: 566-567).

In describing the alpha-amylase variants of the present invention, the nomenclature described below is adapted for ease of reference. The accepted IUPAC single letter or three letter amino acid abbreviation is employed.

Substitutions. For an amino acid substitution, the following nomenclature is used: Original amino acid, position, substituted amino acid. Accordingly, the substitution of threonine with alanine at position 226 is designated as "Thr226Ala" or "T226A". Multiple mutations are separated by addition marks ("+"), e.g., "Gly205Arg+Ser411Phe" or "G205R+S411F", representing substitutions at positions 205 and 411 of glycine (G) with arginine (R) and serine (S) with phenylalanine (F), respectively.

Deletions. For an amino acid deletion, the following nomenclature is used: Original amino acid, position*. Accordingly, the deletion of glycine at position 195 is designated as "Gly195*" or "G195". Multiple deletions are separated by addition marks ("+"), e.g., "Gly195*+Ser411*" or "G195*+S411*".

Insertions. For an amino acid insertion, the following nomenclature is used: Original amino acid, position, original amino acid, inserted amino acid. Accordingly the insertion of lysine after glycine at position 195 is designated "Gly195GlyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
|---|---|
| 195 | 195 195a 195b |
| G | G-K-A |

Multiple alterations. Variants comprising multiple alterations are separated by addition marks ("+"), e.g., "Arg170Tyr+Gly195Glu" or "R170Y+G195E" representing a substitution of tyrosine and glutamic acid for arginine and glycine at positions 170 and 195, respectively.

Different substitutions. Where different substitutions can be introduced at a position, the different substitutions are separated by a comma, e.g., "Arg170Tyr,Glu" represents a substitution of arginine with tyrosine or glutamic acid at position 170. Thus, "Tyr167Gly,Ala+Arg170Gly,Ala" designates the following variants:
"Tyr167Gly+Arg170Gly", "Tyr167Gly+Arg70Ala", "Tyr167Ala+Arg170Gly", and "Tyr167Ala+Arg170Ala".

Parent Alpha-Amylases

The parent alpha-amylase may be a polypeptide with at least 80% sequence identity with the mature polypeptide of SEQ ID NO: 1.

In an aspect, the parent has a sequence identity to the mature polypeptide of SEQ ID NO: 1 of at least 80%, e.g., at least 85%, at least 87%, at least 90%, at least 95%, at least 96%, at least 97%, at least 98%, at least 99%, or 100%, which have alpha-amylase activity. In one aspect, the amino acid sequence of the parent differs by no more than ten amino acids, e.g., by five amino acids, by four amino acids, by three amino acids, by two amino acids, and by one amino acid from the mature polypeptide of SEQ ID NO: 1.

The parent preferably comprises or consists of the amino acid sequence of SEQ ID NO: 1. In another aspect, the parent comprises or consists of the mature polypeptide of SEQ ID NO: 1.

In another embodiment, the parent is an allelic variant of the mature polypeptide of SEQ ID NO: 1.

The parent alpha-amylase may also be a polypeptide with at least 80% sequence identity with the mature polypeptide of SEQ ID NO: 2.

In another aspect, the parent has a sequence identity to the mature polypeptide of SEQ ID NO: 2 of at least 80%, e.g., at least 85%, at least 87%, at least 90%, at least 95%, at least 96%, at least 97%, at least 98%, at least 99%, or 100%, which have alpha-amylase activity. In one aspect, the amino acid sequence of the parent differs by no more than ten amino acids, e.g., by five amino acids, by four amino acids, by three amino acids, by two amino acids, and by one amino acid from the mature polypeptide of SEQ ID NO: 2.

The parent preferably comprises or consists of the amino acid sequence of SEQ ID NO: 2. In another aspect, the parent comprises or consists of the mature polypeptide of SEQ ID NO: 2.

In another embodiment, the parent is an allelic variant of the mature polypeptide of SEQ ID NO: 2.

The parent alpha-amylase may also be a polypeptide with at least 80% sequence identity with the mature polypeptide of SEQ ID NO: 3.

In another aspect, the parent has a sequence identity to the mature polypeptide of SEQ ID NO: 3 of at least 80%, e.g., at least 85%, at least 87%, at least 90%, at least 95%, at least 96%, at least 97%, at least 98%, at least 99%, or 100%, which have alpha-amylase activity. In one aspect, the amino acid sequence of the parent differs by no more than ten amino acids, e.g., by five amino acids, by four amino acids, by three amino acids, by two amino acids, and by one amino acid from the mature polypeptide of SEQ ID NO: 3.

The parent preferably comprises or consists of the amino acid sequence of SEQ ID NO: 3. In another aspect, the parent comprises or consists of the mature polypeptide of SEQ ID NO: 3.

In another embodiment, the parent is an allelic variant of the mature polypeptide of SEQ ID NO: 3.

The parent alpha-amylase may also be a polypeptide with at least 80% sequence identity with the mature polypeptide of SEQ ID NO: 4.

In another aspect, the parent has a sequence identity to the mature polypeptide of SEQ ID NO: 4 of at least 80%, e.g., at least 85%, at least 87%, at least 90%, at least 95%, at least 96%, at least 97%, at least 98%, at least 99%, or 100%, which have alpha-amylase activity. In one aspect, the amino acid sequence of the parent differs by no more than ten amino acids, e.g., by five amino acids, by four amino acids, by three amino acids, by two amino acids, and by one amino acid from the mature polypeptide of SEQ ID NO: 4.

The parent preferably comprises or consists of the amino acid sequence of SEQ ID NO: 4. In another aspect, the parent comprises or consists of the mature polypeptide of SEQ ID NO: 4.

In another embodiment, the parent is an allelic variant of the mature polypeptide of SEQ ID NO: 4.

The parent alpha-amylase may also be a polypeptide with at least 80% sequence identity with the mature polypeptide of SEQ ID NO: 5.

In another aspect, the parent has a sequence identity to the mature polypeptide of SEQ ID NO: 5 of at least 80%, e.g., at least 85%, at least 87%, at least 90%, at least 95%, at least 96%, at least 97%, at least 98%, at least 99%, or 100%, which have alpha-amylase activity. In one aspect, the amino acid sequence of the parent differs by no more than ten amino acids, e.g., by five amino acids, by four amino acids, by three amino acids, by two amino acids, and by one amino acid from the mature polypeptide of SEQ ID NO: 5.

The parent preferably comprises or consists of the amino acid sequence of SEQ ID NO: 5. In another aspect, the parent comprises or consists of the mature polypeptide of SEQ ID NO: 5.

In another embodiment, the parent is an allelic variant of the mature polypeptide of SEQ ID NO: 5.

The parent alpha-amylase may also be a polypeptide with at least 80% sequence identity with the mature polypeptide of SEQ ID NO: 6.

In another aspect, the parent has a sequence identity to the mature polypeptide of SEQ ID NO: 6 of at least 80%, e.g., at least 85%, at least 87%, at least 90%, at least 95%, at least 96%, at least 97%, at least 98%, at least 99%, or 100%, which have alpha-amylase activity. In one aspect, the amino acid sequence of the parent differs by no more than ten amino acids, e.g., by five amino acids, by four amino acids, by three amino acids, by two amino acids, and by one amino acid from the mature polypeptide of SEQ ID NO: 6.

The parent preferably comprises or consists of the amino acid sequence of SEQ ID NO: 6. In another aspect, the parent comprises or consists of the mature polypeptide of SEQ ID NO: 6.

In another embodiment, the parent is an allelic variant of the mature polypeptide of SEQ ID NO: 6.

The parent alpha-amylase may also be a polypeptide with at least 80% sequence identity with the mature polypeptide of SEQ ID NO: 7.

In another aspect, the parent has a sequence identity to the mature polypeptide of SEQ ID NO: 7 of at least 80%, e.g., at least 85%, at least 87%, at least 90%, at least 95%, at least 96%, at least 97%, at least 98%, at least 99%, or 100%, which have alpha-amylase activity. In one aspect, the amino acid sequence of the parent differs by no more than ten amino acids, e.g., by five amino acids, by four amino acids, by three amino acids, by two amino acids, and by one amino acid from the mature polypeptide of SEQ ID NO: 7.

The parent preferably comprises or consists of the amino acid sequence of SEQ ID NO: 7. In another aspect, the parent comprises or consists of the mature polypeptide of SEQ ID NO: 7.

In another embodiment, the parent is an allelic variant of the mature polypeptide of SEQ ID NO: 7.

The parent alpha-amylase may also be a polypeptide with at least 80% sequence identity with the mature polypeptide of SEQ ID NO: 8.

In another aspect, the parent has a sequence identity to the mature polypeptide of SEQ ID NO: 8 of at least 80%, e.g., at least 85%, at least 87%, at least 90%, at least 95%, at least 96%, at least 97%, at least 98%, at least 99%, or 100%, which have alpha-amylase activity. In one aspect, the amino acid sequence of the parent differs by no more than ten amino acids, e.g., by five amino acids, by four amino acids, by three amino acids, by two amino acids, and by one amino acid from the mature polypeptide of SEQ ID NO: 8.

The parent preferably comprises or consists of the amino acid sequence of SEQ ID NO: 8. In another aspect, the parent comprises or consists of the mature polypeptide of SEQ ID NO: 8.

In another embodiment, the parent is an allelic variant of the mature polypeptide of SEQ ID NO: 8.

The parent alpha-amylase may also be a polypeptide with at least 80% sequence identity with the mature polypeptide of SEQ ID NO: 9.

In another aspect, the parent has a sequence identity to the mature polypeptide of SEQ ID NO: 9 of at least 80%, e.g., at least 85%, at least 87%, at least 90%, at least 95%, at least 96%, at least 97%, at least 98%, at least 99%, or 100%, which have alpha-amylase activity. In one aspect, the amino acid sequence of the parent differs by no more than ten amino acids, e.g., by five amino acids, by four amino acids, by three amino acids, by two amino acids, and by one amino acid from the mature polypeptide of SEQ ID NO: 9.

The parent preferably comprises or consists of the amino acid sequence of SEQ ID NO: 9. In another aspect, the parent comprises or consists of the mature polypeptide of SEQ ID NO: 9.

In another embodiment, the parent is an allelic variant of the mature polypeptide of SEQ ID NO: 9.

The parent alpha-amylase may also be a polypeptide with at least 80% sequence identity with the mature polypeptide of SEQ ID NO: 10.

In another aspect, the parent has a sequence identity to the mature polypeptide of SEQ ID NO: 10 of at least 80%, e.g., at least 85%, at least 87%, at least 90%, at least 95%, at least 96%, at least 97%, at least 98%, at least 99%, or 100%, which have alpha-amylase activity. In one aspect, the amino acid sequence of the parent differs by no more than ten amino acids, e.g., by five amino acids, by four amino acids, by three amino acids, by two amino acids, and by one amino acid from the mature polypeptide of SEQ ID NO: 10.

The parent preferably comprises or consists of the amino acid sequence of SEQ ID NO: 10. In another aspect, the parent comprises or consists of the mature polypeptide of SEQ ID NO: 10.

In another embodiment, the parent is an allelic variant of the mature polypeptide of SEQ ID NO: 10.

The parent alpha-amylase may also be a polypeptide with at least 80% sequence identity with the mature polypeptide of SEQ ID NO: 11.

In another aspect, the parent has a sequence identity to the mature polypeptide of SEQ ID NO: 11 of at least 80%, e.g., at least 85%, at least 87%, at least 90%, at least 95%, at least 96%, at least 97%, at least 98%, at least 99%, or 100%, which have alpha-amylase activity. In one aspect, the amino acid sequence of the parent differs by no more than ten amino acids, e.g., by five amino acids, by four amino acids, by three amino acids, by two amino acids, and by one amino acid from the mature polypeptide of SEQ ID NO: 11.

The parent preferably comprises or consists of the amino acid sequence of SEQ ID NO: 11. In another aspect, the parent comprises or consists of the mature polypeptide of SEQ ID NO: 11.

In another embodiment, the parent is an allelic variant of the mature polypeptide of SEQ ID NO: 11.

The parent alpha-amylase may also be a polypeptide with at least 80% sequence identity with the mature polypeptide of SEQ ID NO: 12.

In another aspect, the parent has a sequence identity to the mature polypeptide of SEQ ID NO: 12 of at least 80%, e.g., at least 85%, at least 87%, at least 90%, at least 95%, at least 96%, at least 97%, at least 98%, at least 99%, or 100%, which have alpha-amylase activity. In one aspect, the amino acid sequence of the parent differs by no more than ten amino acids, e.g., by five amino acids, by four amino acids, by three amino acids, by two amino acids, and by one amino acid from the mature polypeptide of SEQ ID NO: 12.

The parent preferably comprises or consists of the amino acid sequence of SEQ ID NO: 12. In another aspect, the parent comprises or consists of the mature polypeptide of SEQ ID NO: 12.

In another embodiment, the parent is an allelic variant of the mature polypeptide of SEQ ID NO: 12.

The amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, or a fragment thereof, may be used to design nucleic acid probes to identify and clone DNA encoding a parent from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other organisms may be screened for DNA that hybridizes with the probes described above and encodes a parent. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material, which is used in a Southern blot.

For purposes of the present invention, hybridization indicates that the polynucleotide hybridizes to a labeled nucleotide probe corresponding to a polynucleotide encoding SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, or a subsequence thereof, under low to very high stringency conditions. Molecules to which the probe hybridizes can be detected using, for example, X-ray film or any other detection means known in the art.

In one aspect, the nucleic acid probe is a polynucleotide that encodes the polypeptide of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, or a fragment thereof.

For long probes of at least 100 nucleotides in length, very low to very high stringency conditions are defined as prehybridization and hybridization at 42° C. in 5×SSPE, 0.3% SDS, 200 micrograms/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally. The carrier material is finally washed three times each for 15 minutes using 2×SSC, 0.2% SDS at 45° C. (very low stringency), 50° C. (low stringency), 55° C. (medium stringency), 60° C. (medium-high stringency), 65° C. (high stringency), or 70° C. (very high stringency).

For short probes that are about 15 nucleotides to about 70 nucleotides in length, stringency conditions are defined as prehybridization and hybridization at about 5° C. to about 10° C. below the calculated $T_m$ using the calculation according to Bolton and McCarthy (1962, *Proc. Natl. Acad. Sci. USA* 48: 1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally. The carrier material is finally washed once in 6×SCC plus 0.1% SDS for 15 minutes and twice each for 15 minutes using 6×SSC at 5° C. to 10° C. below the calculated $T_m$.

The parent may be obtained from microorganisms of any genus. For purposes of the present invention, the term "obtained from" as used herein in connection with a given source shall mean that the parent encoded by a polynucleotide is produced by the source or by a cell in which the polynucleotide from the source has been inserted. In one aspect, the parent is secreted extracellularly.

The parent may be a bacterial alpha-amylase. For example, the parent may be a gram-positive bacterial polypeptide such as a *Bacillus, Clostridium, Enterococcus, Geobacillus, Lactobacillus, Lactococcus, Oceanobacillus, Staphylococcus, Streptococcus,* or *Streptomyces* alpha-amylase, or a gram-negative bacterial polypeptide such as a *Campylobacter, E. coli, Flavobacterium, Fusobacterium, Helicobacter, Ilyobacter, Neisseria, Pseudomonas, Salmonella,* or *Ureaplasma* alpha-amylase.

In one aspect, the parent is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis* alpha-amylase.

In another aspect, the parent is a *Streptococcus equisimilis, Streptococcus pyogenes, Streptococcus uberis,* or *Streptococcus equi* subsp. *Zooepidemicus* alpha-amylase.

In another aspect, the parent is a *Streptomyces achromogenes, Streptomyces avermitilis, Streptomyces coelicolor, Streptomyces griseus,* or *Streptomyces lividans* alpha-amylase.

The parent may be a fungal alpha-amylase. For example, the parent may be a yeast alpha-amylase such as a *Candida, Kluyveromyces, Pichia, Saccharomyces, Schizosaccharomyces,* or *Yarrowia* alpha-amylase. For example, the parent may be a filamentous fungal alpha-amylase such as an *Acremonium, Agaricus, Altemaria, Aspergillus, Aureobasidium, Botyospaeria, Ceriporiopsis, Chaetomidium, Chysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella,* or *Xylaria* alpha-amylase.

In another aspect, the parent is a *Saccharomyces cadsbergensis, Saccharomyces cerevisiae, Saccharomyces diastaticus, Saccharomyces douglasii, Saccharomyces kluyveri, Saccharomyces norbensis,* or *Saccharomyces oviformis* alpha-amylase.

In another aspect, the parent is an *Acremonium cellulolyticus, Aspergillus aculeatus, Aspergillus awamori, Aspergillus foetidus, Aspergillus fumigatus, Aspergillus japonicus, Aspergillus nidulans, Aspergillus niger, Aspergillus oryzae, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia setosa, Thielavia spededonium, Thielavia subthermophila, Thielavia terrestris, Trichoderma harzianum, Trichoderma koningii, Trichoderma longibrachiatum, Trichoderma reesei,* or *Trichoderma viride* alpha-amylase.

In another aspect, the parent is a *Bacillus* sp. alpha-amylase, e.g., the alpha-amylase of SEQ ID NO: 1, SEQ ID NO: 2, SEQ ID NO: 3, SEQ ID NO: 4, SEQ ID NO: 5, or SEQ ID NO: 6.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL).

The parent may be identified and obtained from other sources including microorganisms isolated from nature (e.g., soil, composts, water, etc.) or DNA samples obtained directly from natural materials (e.g., soil, composts, water, etc) using the above-mentioned probes. Techniques for isolating microorganisms and DNA directly from natural habitats are well known in the art. The polynucleotide encoding a parent may then be derived by similarly screening a genomic or cDNA library of another microorganism or mixed DNA sample. Once a polynucleotide encoding a parent has been detected with a probe(s), the polynucleotide may be isolated or cloned by utilizing techniques that are known to those of ordinary skill in the art (see, e.g., Sambrook et al., 1989, supra).

The parent may be a hybrid polypeptide in which a portion of one polypeptide is fused at the N-terminus or the C-terminus of a portion of another polypeptide.

The parent may also be a fused polypeptide or cleavable fusion polypeptide in which one polypeptide is fused at the N-terminus or the C-terminus of another polypeptide. A fused polypeptide is produced by fusing a polynucleotide encoding one polypeptide to a polynucleotide encoding another polypeptide. Techniques for producing fusion polypeptides are known in the art, and include ligating the coding sequences encoding the polypeptides so that they are in frame and that expression of the fused polypeptide is under control of the same promoter(s) and terminator. Fusion proteins may also be constructed using intein technology in which fusions are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Preparation of Variants

The present invention also relates to methods for obtaining a variant having alpha-amylase activity, comprising: (a) introducing into a parent alpha-amylase an alteration at two or more (several) positions corresponding to positions 140, 181, 189, 134, 195, 206, 243, 260, 262, 284, 304, 347, 439, 469, 476 and 477 of the mature polypeptide of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, or SEQ ID NO: 12, wherein the numbering is according to SEQ ID NO 1 and the variant has alpha-amylase activity; and (b) recovering the variant.

In in one aspect the invention relates to a method for obtaining a variant having alpha-amylase activity, comprising: (a) introducing into a parent alpha-amylase an alteration at two or more (several) positions corresponding to W140, R181, W189, D134, N195, V206, Y243, E260, F262, W284, G304, W347, W439, W469, G476, and G477 of the mature polypeptide of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, or SEQ ID NO: 12, wherein the numbering is according to SEQ ID NO 1 and the variant has alpha-amylase activity; and (b) recovering the variant.

In one embodiment the introduced alteration is a substitution.

In yet another embodiment the invention relates to a method for obtaining a variant having alpha-amylase activity, comprising: (a) introducing into a parent alpha-amylase a substitution at two or more (several) positions corresponding to G304RKEQ, W140YF, W189EGT, D134E, E260ADCQLMFPSWVGHIKNRTY, F262GP, W284DHFYR, W347HFY, W439RG, G476EQRK, G477EQKMR of the mature polypeptide of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, or SEQ ID NO: 12, wherein the numbering is according to SEQ ID NO 1 and the variant has alpha-amylase activity; and (b) recovering the variant.

In a preferred embodiment, the introduced substitutions are two or more of G304R, W140YF, W189EGT, D134E, E260GHIKNRTY, W284DFR, W439RG, G476EK, G477EKMR. In a more preferred embodiment, the introduced substitutions are G304R, W140YF, E260GHIKNPRTY and G476EQRK. In an even more preferred embodiment, the method for obtaining a variant having alpha-amylase activity, comprisises: (a) introducing into a parent alpha-amylase substitutions of G304R, W140Y, E260G and G476K in any of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, or SEQ ID NO: 12, wherein the numbering is according to SEQ ID NO 1 and the variant has alpha-amylase activity; and (b) recovering the variant. The variants can be prepared using any mutagenesis procedure known in the art, such as site-directed mutagenesis, synthetic gene construction, semi-synthetic gene construction, random mutagenesis, shuffling, etc.

Site-directed mutagenesis is a technique in which one or more (several) mutations are created at one or more defined sites in a polynucleotide encoding the parent.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests at the plasmid and the oligonucleotide is the same, permitting sticky ends of the plasmid and insert to ligate to one another. See, e.g., Scherer and Davis, 1979, *Proc. Natl. Acad. Sci. USA* 76: 4949-4955; and Barton et al., 1990, *Nucleic Acids* Res. 18: 7349-4966.

Site-directed mutagenesis can also be accomplished in vivo by methods known in the art. See, e.g., U.S. Patent Application Publication No. 2004/0171154; Storici et al., 2001, *Nature Biotechnol.* 19: 773-776; Kren et al., 1998, *Nat. Med.* 4: 285-290; and Calissano and Macino, 1996, *Fungal Genet. Newslett.* 43: 15-16.

Any site-directed mutagenesis procedure can be used in the present invention. There are many commercial kits available that can be used to prepare variants.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, *Nature* 432: 1050-1054) and similar technologies wherein olgionucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204) and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

Variants

The present invention also provides variants of a parent alpha-amylase comprising an alteration at two or more (several) positions corresponding to positions G304, W140, W189, D134, E260, F262, W284, W347, W439, W469, G476, and G477 of the mature polypeptide of SEQ ID NO: 1, and wherein each alteration is independently a substitution, insertion or deletion (preferably a substitution) and the variant has alpha-amylase activity. Hereby, variants are provided which has improved washing performance at low temperature, compared to the parent alpha-amylase or compared to the alpha-amylase of SEQ ID NO: 1, 2, 3, 4, 5, 6, 7, 8, 9, 10, 11 or 12.

In an embodiment, the variant has sequence identity of at least 80%, e.g., at least 85%, at least 90%, at least 95%, at least 96%, at least 97%, at least 98%, or at least 99%, but less than 100%, to the amino acid sequence of the parent alpha-amylase.

In another embodiment, the invention relates to isolated variants of an alpha-amylase, comprising an alteration at two or more (several) positions corresponding to positions G304, W140, W189, D134, E260, F262, W284, W347, W439, W469, G476, and G477 of the mature polypeptide of SEQ ID NO: 1, wherein each alteration is independently a substitution, deletion or insertion, and wherein the variant has at least 80% but less than 100% sequence identity with the mature polypeptide of any of SEQ ID NOs 1, 2, 3, 4, 5, 6, 7, 8, 9, 10, 11 or 12, and wherein the variant has alpha-amylase activity.

In another embodiment, the variant has at least 85%, at least 87%, at least 90%, at least 95%, such as at least 96%, at least 97%, at least 98%, and at least 99%, but less than 100%, sequence identity with the mature polypeptide of SEQ ID NO: 1.

In another embodiment, the variant has at least at least 85%, at least 87%, at least 90%, at least 95%, such as at least 96%, at least 97%, at least 98%, and at least 99%, but less than 100%, sequence identity with the mature polypeptide of SEQ ID NO: 2.

In another embodiment, the variant has at least 85%, at least 87%, at least 90%, at least 95%, such as at least 96%, at least 97%, at least 98%, and at least 99%, but less than 100%, sequence identity with the mature polypeptide of SEQ ID NO: 3.

In another embodiment, the variant has at least 85%, at least 87%, at least 90%, at least 95%, such as at least 96%, at least 97%, at least 98%, and at least 99%, but less than 100%, sequence identity with the mature polypeptide of SEQ ID NO: 4.

In another embodiment, the variant has at least 85%, at least 87%, at least 90%, at least 95%, such as at least 96%, at least 97%, at least 98%, and at least 99%, but less than 100%, sequence identity with the mature polypeptide of SEQ ID NO: 5.

In another embodiment, the variant has at least 85%, at least 87%, at least 90%, at least 95%, such as at least 96%, at least 97%, at least 98%, and at least 99%, but less than 100%, sequence identity with the mature polypeptide of SEQ ID NO: 6.

In another embodiment, the variant has at least 85%, at least 87%, at least 90%, at least 95%, such as at least 96%, at least 97%, at least 98%, and at least 99%, but less than 100%, sequence identity with the mature polypeptide of SEQ ID NO: 7.

In another embodiment, the variant has at least 85%, at least 87%, at least 90%, at least 95%, such as at least 96%, at least 97%, at least 98%, and at least 99%, but less than 100%, sequence identity with the mature polypeptide of SEQ ID NO: 8.

In another embodiment, the variant has at least 85%, at least 87%, at least 90%, at least 95%, such as at least 96%, at least 97%, at least 98%, and at least 99%, but less than 100%, sequence identity with the mature polypeptide of SEQ ID NO: 9.

In another embodiment, the variant has at least 85%, at least 87%, at least 90%, at least 95%, such as at least 96%, at least 97%, at least 98%, and at least 99%, but less than 100%, sequence identity with the mature polypeptide of SEQ ID NO: 10.

In another embodiment, the variant has at least 85%, at least 87%, at least 90%, at least 95%, such as at least 96%, at least 97%, at least 98%, and at least 99%, but less than 100%, sequence identity with the mature polypeptide of SEQ ID NO: 11.

In another embodiment, the variant has at least 85%, at least 87%, at least 90%, at least 95%, such as at least 96%, at least 97%, at least 98%, and at least 99%, but less than 100%, sequence identity with the mature polypeptide of SEQ ID NO: 12.

In one aspect, the number of alterations in the variants of the present invention is 2-20, e.g., 2-10 and 2-5, such as 2, 3, 4, 5, 6, 7, 8, 9 or 10 alterations.

In one aspect, a variant comprises an alteration at two or more (several) positions corresponding to positions G304, W140, W189, D134, E260, F262, W284, W347, W439, W469, G476, and G477. In another aspect, a variant comprises an alteration at two positions corresponding to any of positions G304, W140, W189, D134, E260, F262, W284, W347, W439, W469, G476, and G477. In another aspect, a variant comprises an alteration at three positions corresponding to any of positions G304, W140, W189, D134, E260, F262, W284, W347, W439, W469, G476, and G477. In another aspect, a variant comprises an alteration at four positions corresponding to any of positions G304, W140, W189, D134, E260, F262, W284, W347, W439, W469, G476, and G477. In another aspect, a variant comprises an alteration at five positions corresponding to any of positions G304, W140, W189, D134, E260, F262, W284, W347, W439, W469, G476, and G477. In another aspect, a variant comprises an alteration at six positions corresponding to any of positions G304, W140, W189, D134, E260, F262, W284, W347, W439, W469, G476, and G477. In another aspect, a variant comprises an alteration at each position corresponding to positions G304, W140, W189, D134, E260, F262, W284, W347, W439, W469, G476, and G477. The positions correspond to the positions of SEQ ID NO: 1. It is preferred that the alterations are substitutions.

In one embodiment, the variant comprises a substitution at two, three or four positions selected from the group consisting of G304, W140, W189, D134, E260, F262, W284, W347, W439, W469, G476, and G477.

In a preferred embodiment, the variant comprises a substitution at two, three or four positions selected from the group consisting of G304, W140, E260 and G476.

In one aspect of the invention, the variant comprises two or more (several) substitutions selected from the group consisting of G304RKEQ, W140YF, W189EGT, D134E, E260ADCQLMFPSWVGHIKNRTY, F262GP, W284DHFYR, W347HFY, W439RG, G476EQRK, G477EQKMR.

It is preferred that the variant according to the invention comprises substitutions at two, three or four positions selected from the group consisting of G304R, W140YF, E260GHIKNPRTY and G476EQRK. In a more preferred embodiment, the substitutions at the two, three or four positions are selected from the group consisting of G304R, W140Y, E260G and G476K.

In one embodiment, the variant further comprises one or more substitutions selected from the group consisting of T51IL, S52Q, N54K, G109A, E194D, N195F, V206Y, Y243F, G109A, G273DV, G337N, K72R, R181H, S303G and Y100I. In a preferred embodiment the one or more further substitutions are selected from the group consisting of N195F, V206Y, Y243F. Preferably, the variant comprises two or three of these substitutions. Hereby, variants are provided that have improved wash performance at low temperature as well as improved stability to $Ca^{2+}$ depletion, compared to the parent alpha-amylase or compared to the alpha-amylase of SEQ ID NO: 1, 2, 3, 4, 5, 6, 7, 8, 9, 10, 11 or 12.

In another aspect of the invention, the variant comprises two or more (several) substitutions of the mature polypeptide of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, or SEQ ID NO: 12, selected from the group consisting of D134E, E260G, E260H, E260I, E260K, E260N, E260R, E260T, G109A, G273D, G273V, G337N, G476E, G477E, G477M, G477R, K72R, R181H, S303G, W140F, W140Y, W189E, W189G, W189T, W284D, and Y100I.

The variants may further comprise an alteration at one or more (several) other positions. For example, the variants may comprise an alteration at a position corresponding to positions G182*+D183* or D183*+G184*.

In another aspect, the invention relates to variants which comprise substitutions in the positions, corresponding to the positions of the polypeptide of SEQ ID NO: 1, selected from the group consisting of:
W140Y+N195F+V206Y+Y243F+E260G+G477E,
W140Y+N195F+V206Y+Y243F+E260T+W284D,
W140Y+N195F+V206Y+Y243F+W284D,
G109A+W140Y+N195F+V206Y+Y243F+E260G,
W140Y+N195F+V206Y+Y243F+E260G,
N195F+V206Y+Y243F+E260K+W284D,
D134E+G476E,
W140Y+N195F+V206Y+Y243F+E260G+G476E,
W140Y+W189G+N195F+V206Y+Y243F+E260G,
W140Y+N195F+V206Y+Y243F+E260G+S303G,
W140Y+W189T+N195F+V206Y+Y243F+E260G,
W140Y+N195F+V206Y+Y243F+E260G+W284D,
Y100I+W140Y+N195F+V206Y+Y243F+E260G,
W140Y+N195F+V206Y+Y243F+E260G+G337N,
W140Y+N195F+V206Y+Y243F+E260G+W439R
G109A+W140Y+E194D+N195F+V206Y+Y243F+E260G
G109A+W140Y+N195F+V206Y+Y243F+E260G+G476E
T51I+Y100I+G109A+W140Y+N195F+V206Y+Y243F+
  E260G
T51I+G109A+W140Y+N195F+V206Y+Y243F+E260G+
  W439R
T51I+S52Q+N54K+G109A+W140Y+N195F+V206Y+
  Y243F+E260G+G476E
W140Y+N195F+V206Y+Y243F+E260G+G304R+G476K
W140Y+N195F+V206Y+Y243F+E260G+W284R+G477K
W140Y+N195F+V206Y+Y243F+E260G+W284F+G477R,
  and
N195F+V206Y+Y243F+E260G+W284D.

In another aspect, the invention relates to variants which consist of substitutions in the positions, corresponding to the positions of the polypeptide of SEQ ID NO: 1, selected from the group consisting of:
W140Y+N195F+V206Y+Y243F+E260G+G477E,
W140Y+N195F+V206Y+Y243F+E260T+W284D,
W140Y+N195F+V206Y+Y243F+W284D,
G109A+W140Y+N195F+V206Y+Y243F+E260G,
W140Y+N195F+V206Y+Y243F+E260G,
N195F+V206Y+Y243F+E260K+W284D,
D134E+G476E,
W140Y+N195F+V206Y+Y243F+E260G+G476E,
W140Y+W189G+N195F+V206Y+Y243F+E260G,
W140Y+N195F+V206Y+Y243F+E260G+S303G,
W140Y+W189T+N195F+V206Y+Y243F+E260G,
W140Y+N195F+V206Y+Y243F+E260G+W284D,
Y100I+W140Y+N195F+V206Y+Y243F+E260G,
W140Y+N195F+V206Y+Y243F+E260G+G337N,
W140Y+N195F+V206Y+Y243F+E260G+W439R
G109A+W140Y+E194D+N195F+V206Y+Y243F+E260G
G109A+W140Y+N195F+V206Y+Y243F+E260G+G476E
T51I+Y100I+G109A+W140Y+N195F+V206Y+Y243F+
  E260G
T51I+G109A+W140Y+N195F+V206Y+Y243F+E260G+
  W439R
T51I+S52Q+N54K+G109A+W140Y+N195F+V206Y+
  Y243F+E260G+G476E
W140Y+N195F+V206Y+Y243F+E260G+G304R+G476K
W140Y+N195F+V206Y+Y243F+E260G+W284R+G477K
W140Y+N195F+V206Y+Y243F+E260G+W284F+G477R,
  and
N195F+V206Y+Y243F+E260G+W284D.

In yet another aspect, the invention relates to variants which comprise alterations in the positions, corresponding to the positions of the polypeptide of SEQ ID NO: 1, selected from the group consisting of:
D183*+G184*+W140Y+N195F+V206Y+Y243F+E260G+
  G477E,
D183*+G184*+W140Y+N195F+V206Y+Y243F+E260T+
  W284D,
D183*+G184*+W140Y+N195F+V206Y+Y243F+W284D,
D183*+G184*+G109A+W140Y+N195F+V206Y+Y243F+
  E260G,
D183*+G184*+W140Y+N195F+V206Y+Y243F+E260G,
D183*+G184*+N195F+V206Y+Y243F+E260K+W284D,
D183*+G184*+D134E+G476E,
D183*+G184*+W140Y+N195F+V206Y+Y243F+E260G+
  G476E,
D183*+G184*+W140Y+W189G+N195F+V206Y+
  Y243F+E260G,
D183*+G184*+W140Y+N195F+V206Y+Y243F+E260G+
  S303G,
D183*+G184*+W140Y+W189T+N195F+V206Y+
  Y243F+E260G,
D183*+G184*+W140Y+N195F+V206Y+Y243F+E260G+
  W284D,
D183*+G184*+Y100I+W140Y+N195F+V206Y+Y243F+
  E260G,
D183*+G184*+W140Y+N195F+V206Y+Y243F+E260G+
  G337N,
D183*+G184*+W140Y+N195F+V206Y+Y243F+E260G+
  W439R
D183*+G184*+G109A+W140Y+E194D+N195F+V206Y+
  Y243F+E260G
D183*+G184*+G109A+W140Y+N195F+V206Y+Y243F+
  E260G+G476E
D183*+G184*+T51I+Y100I+G109A+W140Y+N195F+
  V206Y+Y243F+E260G
D183*+G184*+T51I+G109A+W140Y+N195F+V206Y+
  Y243F+E260G+W439R
D183*+G184*+T51I+S52Q+N54K+G109A+W140Y+
  N195F+V206Y+Y243F+E260G+G476E
D183*+G184*+W140Y+N195F+V206Y+Y243F+E260G+
  G304R+G476K
D183*+G184*+W140Y+N195F+V206Y+Y243F+E260G+
  W284R+G477K
D183*+G184*+W140Y+N195F+V206Y+Y243F+E260G+
  W284F+G477R, and
D183*+G184*+N195F+V206Y+Y243F+E260G+W284D.

In another aspect, the invention relates to variants which consist of alterations in the positions, corresponding to the positions of the polypeptide of SEQ ID NO: 1, selected from the group consisting of:

D183*+G184*+W140Y+N195F+V206Y+Y243F+E260G+ G477E,
D183*+G184*+W140Y+N195F+V206Y+Y243F+E260T+ W284D,
D183*+G184*+W140Y+N195F+V206Y+Y243F+W284D,
D183+G184*+G109A+W140Y+N195F+V206Y+Y243F+ E260G,
D183*+G184*+W140Y+N195F+V206Y+Y243F+E260G,
D183*+G184*+N195F+V206Y+Y243F+E260K+W284D,
D183*+G184*+D134E+G476E,
D183*+G184*+W140Y+N195F+V206Y+Y243F+E260G+ G476E,
D183*+G184*+W140Y+W189G+N195F+V206Y+ Y243F+E260G,
D183*+G184*+W140Y+N195F+V206Y+Y243F+E260G+ S303G,
D183*+G184*+W140Y+W189T+N195F+V206Y+ Y243F+E260G,
D183*+G184*+W140Y+N195F+V206Y+Y243F+E260G+ W284D,
D183*+G184*+Y100I+W140Y+N195F+V206Y+Y243F+ E260G,
D183*+G184*+W140Y+N195F+V206Y+Y243F+E260G+ G337N,
D183*+G184*+W140Y+N195F+V206Y+Y243F+E260G+ W439R
D183*+G184*+G109A+W140Y+E194D+N195F+V206Y+ Y243F+E260G
D183*+G184*+G109A+W140Y+N195F+V206Y+Y243F+ E260G+G476E
D183*+G184*+T51I+Y100I+G

Aspergilli; non-limiting examples include modified promoters including the gene encoding neutral alpha-amylase in *Aspergillus niger* in which the untranslated leader has been replaced by an untranslated leader from the gene encoding triose phosphate isomerase in *Aspergillus nidulans* or *Aspergillus oryzae*); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, which is recognized by a host cell to terminate transcription. The terminator sequence is operably linked to the 3'-terminus of the polynucleotide encoding the variant. Any terminator that is functional in the host cell may be used.

Preferred terminators for filamentous fungal host cells are obtained from the genes for *Aspergillus nidulans* anthranilate synthase, *Aspergillus niger* alpha-glucosidase, *Aspergillus niger* glucoamylase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA that is important for translation by the host cell. The leader sequence is operably linked to the 5'-terminus of the polynucleotide encoding the variant. Any leader sequence that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the variant-encoding sequence and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a variant and directs the variant into the cell's secretory pathway. The 5'-end of the coding sequence of the polynucleotide may inherently contain a signal peptide coding region naturally linked in translation reading frame with the segment of the coding region that encodes the variant. Alternatively, the 5'-end of the coding sequence may contain a signal peptide coding region that is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the variant. However, any signal peptide coding region that directs the expressed variant into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding region that encodes a propeptide positioned at the N-terminus of a variant. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide regions are present at the N-terminus of a variant, the propeptide region is positioned next to the N-terminus of the variant and the signal peptide region is positioned next to the N-terminus of the propeptide region.

It may also be desirable to add regulatory sequences that allow the regulation of the expression of the variant relative to the growth of the host cell. Examples of regulatory systems are those that cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the variant would be operably linked with the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more (several) convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about the expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more (several) selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are the dal genes from *Bacillus licheniformis* or *Bacillus subtilis*, or markers that confer antibiotic resistance such as ampicillin, chloramphenicol, kanamycin, or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vector preferably contains an element(s) that permits integration of the vector into the host cell's genome or autonomous replication of the vector in the cell independent of the genome.

For integration into the host cell genome, the vector may rely on the polynucleotide's sequence encoding the variant or any other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of identity to the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a nucleotide sequence that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMß1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into the host cell to increase production of a variant. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra) to obtain substantially pure variants.

Host Cells

The present invention also relates to recombinant host cells, comprising a polynucleotide of the present invention operably linked to one or more (several) control sequences that direct the production of a variant of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the variant and its source.

The host cell may be any cell useful in the recombinant production of a variant, e.g., a prokaryote or a eukaryote.

The prokaryotic host cell may be any gram-positive or gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell, including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell, including, but not limited to, *Streptococcus equisimilis, Streptococcus pyogenes, Streptococcus ubens*, and *Streptococcus equi* subsp. *Zooepidemicus* cells.

The bacterial host cell may also be any *Streptomyces* cell, including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may, for instance, be effected by protoplast transformation (see, e.g., Chang and Cohen, 1979, *Mol. Gen. Genet.* 168: 111-115), by using competent cells (see, e.g., Young and Spizizen, 1961, *J. Bacteriol.* 81: 823-829, or Dubnau and Davidoff-Abelson, 1971, *J. Mol. Biol.* 56: 209-221), by electroporation (see, e.g., Shigekawa and Dower, 1988, *Biotechniques* 6: 742-751), or by conjugation (see, e.g., Koehler and Thome, 1987, *J. Bacteriol.* 169: 5271-5278). The introduction of DNA into an *E. coli* cell may, for instance, be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may, for instance, be effected by protoplast transformation and electroporation (see, e.g., Gong et al., 2004, *Folia Microbiol.* (Praha) 49: 399-405), by conjugation (see, e.g., Mazodier et al., 1989, J. Bacteriol. 171: 3583-3585), or by transduction (see, e.g., Burke et al., 2001, *Proc. Natl. Acad. Sci. USA* 98: 6289-6294). The introduction of DNA into a *Pseudomonas* cell may, for instance, be effected by electroporation (see, e.g., Choi et al., 2006, *J. Microbiol. Methods* 64: 391-397) or by conjugation (see, e.g., Pinedo and Smets, 2005, *Appl. Environ. Microbiol.* 71: 51-57). The introduction of DNA into a *Streptococcus* cell may, for instance, be effected by natural competence (see, e.g., Perry and Kuramitsu, 1981, *Infect. Immun.* 32: 1295-1297), by protoplast transformation (see, e.g., Catt and Jollick, 1991, *Microbios* 68: 189-2070, by electroporation (see, e.g., Buckley et al., 1999, *Appl. Environ. Microbiol.* 65: 3800-3804) or by conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980).

The yeast host cell may be a *Candida, Hansenula, Kluyveromyces, Pichia, Saccharomyces, Schizosaccharomyces*, or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chysosporium inops, Chysosporium keratinophilum, Chysosporium lucknowense, Chysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eyngii, Thielavia terrestris, Trametes villosa, Trametes versicolor, Trichoderma*

*harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023 and Yelton et al., 1984, *Proc. Natl. Acad. Sci. USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a variant, comprising: (a) cultivating a host cell of the present invention under conditions suitable for the expression of the variant; and (b) recovering the variant.

The host cells are cultivated in a nutrient medium suitable for production of the variant using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the variant is secreted into the nutrient medium, the variant can be recovered directly from the medium. If the variant is not secreted, it can be recovered from cell lysates.

The variant may be detected using methods known in the art that are specific for the variants. These detection methods may include use of specific antibodies, formation of an enzyme product, or disappearance of an enzyme substrate. For example, an enzyme assay may be used to determine the activity of the variant.

The variant may be recovered by methods known in the art. For example, the variant may be recovered from the nutrient medium by conventional procedures including, but not limited to, collection, centrifugation, filtration, extraction, spray-drying, evaporation, or precipitation.

The variant may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989) to obtain substantially pure variants.

In an alternative aspect, the variant is not recovered, but rather a host cell of the present invention expressing a variant is used as a source of the variant.

Compositions

The present invention also relates to compositions comprising a variant of the present invention. Preferably, the compositions are enriched in such a variant. The term "enriched" means that the alpha-amylase activity of the composition has been increased, e.g., with an enrichment factor of 1.1.

The composition may comprise a variant as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The additional enzyme(s) may be produced, for example, by a microorganism belonging to the genus *Aspergillus*, e.g., *Aspergillus aculeatus, Aspergillus awamori, Aspergillus foetidus, Aspergillus fumigatus, Aspergillus japonicus, Aspergillus nidulans, Aspergillus niger,* or *Aspergillus oryzae; Fusarium*, e.g., *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sulphureum, Fusarium toruloseum, Fusarium trichothecioides,* or *Fusarium venenatum; Humicola*, e.g., *Humicola insolens* or *Humicola lanuginosa*; or *Trichoderma*, e.g., *Trichoderma harzianum, Trichoderma koningii, Trichoderma longibrachiatum, Trichoderma reesei,* or *Trichoderma viride*.

The compositions may be prepared in accordance with methods known in the art and may be in the form of a liquid or a dry composition. For instance, the composition may be in the form of a granulate or a microgranulate. The variant may be stabilized in accordance with methods known in the art.

According to the invention, the above alpha-amylase variants may typically be a component in a cleaning composition, such as a detergent composition, e.g., a laundry detergent composition or a dishwashing detergent composition. Especially preferred is a liquid laundry detergent composition.

Such cleaning compositions comprise a cleaning/detergent adjunct, preferably a mixture of components. Typically the cleaning adjunct will be present in the composition in an amount from 0.001 to 99.9 wt %, more typically from 0.01 to 80 wt % cleaning adjunct.

In another preferred aspect the composition comprises one or more surfactants, which may be non-ionic including semi-polar and/or anionic and/or cationic and/or zwitterionic and/or ampholytic and/or semi-polar nonionic and/or mixtures thereof. The surfactants are typically present at a level of from 0.1% to 60% by weight or from 0.5 to 50 wt % or 1 to 40 wt % of the composition.

Uses

The present invention is also directed to methods for using the alpha-amylase variants. The alpha-amylase variants of the invention are useful in detergent compositions, laundry washing, dishwashing and/or cleaning processes at low temperature.

EXAMPLES pNP-G7 Assay for Determination of Alpha-Amylase Activity

The alpha-amylase activity may be determined by a method employing the G7-pNP substrate. G7-pNP which is an abbreviation for 4,6-ethylidene($G_7$)-p-nitrophenyl($G_1$)-α, D-maltoheptaoside, a blocked oligosaccharide which can be cleaved by an endo-amylase, such as an alpha-amylase. Following the cleavage, the alpha-Glucosidase included in the kit digest the hydrolysed substrate further to liberate a free PNP molecule which has a yellow color and thus can be measured by visible spectophometry at λ=405 nm (400-420 nm). Kits containing G7-pNP substrate and alpha-Glucosidase is manufactured by Roche/Hitachi (cat. No. 11876473).

Reagents:

The G7-pNP substrate from this kit contains 22 mM 4,6-ethylidene-G7-pNP and 52.4 mM HEPES (2-[4-(2-hydroxyethyl)-1-piperazinyl]-ethanesulfonic acid), pH 7.0).

The alpha-Glucosidase reagent contains 52.4 mM HEPES, 87 mM NaCl, 12.6 mM $MgCl_2$, 0.075 mM $CaCl_2$, ≥4 kU/L alpha-glucosidase).

The substrate working solution is made by mixing 1 mL of the alpha-Glucosidase reagent with 0.2 mL of the G7-pNP substrate. This substrate working solution is made immediately before use.

Dilution buffer: 50 mM MOPS, 0.05% (w/v) Triton X100 (polyethylene glycol p-(1,1,3,3-tetramethylbutyl)-phenyl ether ($C_{14}H_{22}O(C_2H_4O)$ (n=9-10))), 1 mM CaCl2, pH8.0.

Procedure:

The amylase sample to be analyzed was diluted in dilution buffer to ensure the pH in the diluted sample is 7. The assay was performed by transferring 20 µl diluted enzyme samples to 96 well microtiter plate and adding 80 µl substrate working solution. The solution was mixed and pre-incubated 1 minute at room temperature and absorption is measured every 20 sec. over 5 minutes at OD 405 nm.

The slope (absorbance per minute) of the time dependent absorption-curve is directly proportional to the specific activity (activity per mg enzyme) of the alpha-amylase in question under the given set of conditions. The amylase sample should be diluted to a level where the slope is below 0.4 absorbance units per minute.

Automatic Mechanical Stress Assay (AMSA) for laundry

In order to assess the wash performance in laundry washing experiments are performed, using the Automatic Mechanical Stress Assay (AMSA). With the AMSA, the wash performance of a large quantity of small volume enzyme-detergent solutions can be examined. The AMSA plate has a number of slots for test solutions and a lid firmly squeezing the laundry sample, the textile to be washed against all the slot openings. During the washing time, the plate, test solutions, textile and lid are vigorously shaken to bring the test solution in contact with the textile and apply mechanical stress in a regular, periodic oscillating manner. For further description see WO02/42740 especially the paragraph "Special method embodiments" at page 23-24.

General Wash Performance Description

A test solution comprising water (10° dH), detergent, e.g. 5.1 g/L European liquid detergent as described below and the enzyme of the invention, e.g. at concentration of 0, 0.8 and/or 1.2 mg enzyme protein/L, is prepared. Fabrics stained with starch (e.g. CS-28 from Center For Testmaterials BV, P.O. Box 120, 3133 KT, Vlaardingen, The Netherlands) is added and washed for 20 minutes at 20° C. After thorough rinse under running tap water and drying in the dark, the light intensity or reflectance values of the stained fabrics are subsequently measured as a measure for wash performance. The test with 0 mg enzyme protein/L is used as a blank to obtain a delta remission value. Preferably mechanical action is applied during the wash step, e.g. in the form of shaking, rotating or stirring the wash solution with the fabrics.

The AMSA wash performance experiments were conducted under the experimental conditions specified below:

TABLE 1

| AMSA experimental conditions | |
| --- | --- |
| Laundry liquid detergent dosage | 5.7 g/L European (EU) liquid detergent (cf. Example 1A), or 0.8 g/L Northern America (US) liquid detergent (cf. Example 1B) |
| Test solution volume | 160 micro L |
| pH | as is |
| Wash time | 20 minutes |
| Temperature | 20° C. |
| Water hardness | 10° dH, $Ca^{2+}:Mg^{2+}:HCO_3^-$ = 3:1:6 |
| Enzyme concentration in test solution | 0.8 and 1.2 Mg/L |
| Test material | CS-28 (Rice starch on cotton) |

Amylase dilution buffer: Amylase was diluted in ultrapure water (MilliQ water) with a small concentration of calcium (0.1 mM) to stabilize the amylase during storage and 0.01% Triton X-100 to reduce risk of adsorption of enzyme protein to containers and pipettes.

Water hardness was adjusted to 10° dH by addition of $CaCl_2$, $MgCl_2$, and $NaHCO_3$ ($Ca^{2+}:Mg^{2+}:HCO_3^-$=3:1:4.5) to the test system. After washing the textiles were flushed in tap water and dried.

The wash performance is measured as the brightness of the colour of the textile washed. Brightness can also be expressed as the intensity of the light reflected from the sample when illuminated with white light. When the sample is stained the intensity of the reflected light is lower, than that of a clean sample. Therefore the intensity of the reflected light can be used to measure wash performance.

Color measurements are made with a professional flatbed scanner (Kodak iQsmart, Kodak, Midtager 29, DK-2605 Brøndby, Denmark), which is used to capture an image of the washed textile.

To extract a value for the light intensity from the scanned images, 24-bit pixel values from the image are converted into values for red, green and blue (RGB). The intensity value (Int) is calculated by adding the RGB values together as vectors and then taking the length of the resulting vector:

$$Int=\sqrt{r^2+g^2+b^2}.$$

Textiles: Textile sample CS-28 (rice starch on cotton) is obtained from Center For Testmaterials BV, P.O. Box 120, 3133 KT Vlaardingen, the Netherlands.

Results of the AMSA laundry test of different variants are shown in Table 3. In the result the index is 100. The performance result of the parent alpha-amylase is assigned the value of 100 and the results of the variants are compared to this value.

AMSA Wash Performance

The wash performance of the variants and corresponding parent alpha-amylases were tested by the AMSA-test method as described in the Methods section. The results are given as (performance of variant minus performance of blank) divided by (performance of parent minus performance of blank) multiplied by 100, where the blank is the performance obtained by washing at the same conditions, but in the absence of alpha-amylase. Finally a mean of relative performance at the two concentrations 0.8 and 1.2 Mg/L were calculated.

Results are presented in Table 3.

Terg-O-Tometer (TOM) Wash Assay

The Tergo-To-Meter (TOM) is a medium scale model wash system that can be applied to test 12 different wash conditions simultaneously. A TOM is basically a large temperature controlled water bath with up to 12 open metal beakers submerged into it. Each beaker constitutes one small top loader style washing machine and during an experiment, each of them will contain a solution of a specific detergent/enzyme system and the soiled and unsoiled fabrics its performance is tested on. Mechanical stress is achieved by a rotating stirring arm, which stirs the liquid within each beaker. Because the TOM beakers have no lid, it is possible to withdraw samples during a TOM experiment and assay for information on-line during wash.

The TOM model wash system is mainly used in medium scale testing of detergents and enzymes at US or LA/AP wash conditions. In a TOM experiment, factors such as the ballast to soil ratio and the fabric to wash liquor ratio can be varied. Therefore, the TOM provides the link between small scale experiments, such as AMSA and mini-wash, and the more time consuming full scale experiments in top loader washing machines.

Equipment: The water bath with 12 steel beakers and 1 rotating arm per beaker with capacity of 500 or 1200 mL of detergent solution. Temperature ranges from 5 to 80° C. The water bath has to be filled up with deionised water. Rotational speed can be set up to 70 to 120 rpm/min.

TOM Wash Performance

Water hardness was adjusted to the strength described below by addition of $CaCl_2$, $MgCl_2$ and $NAHCO_3$. Wash solutions were prepared with desired amount of detergent, temperature and water hardness in a bucket as described below. Detergent was dissolved during magnet stirring for 10 min. (Wash solution was used within 30 to 60 min after preparation).

Temperature and rotation (rpm) in the water bath in the Terg-O-Tometer were set according to the settings below. When temperature was adjusted according to settings (tolerance is +/−0.5° C.) wash solution was added to TOM beaker according to the amount described below.

Agitation in the beaker was at 120 rpm. 2 rice starch swatches (CS-28) and soil ballast were added to each of the beakers and wash carried out according to time stated below. Swatches were rinsed in cold tap water for 5 min. The swatches were left to dry in the dark over night.

Textile: Textile sample CS-28 (rice starch on cotton) was obtained from Center for Testmaterials BV, P.O. Box 120, 3133 KT Vlaardingen, the Netherlands.

Soil ballast: Soil ballast Rice starch on cotton/polyester (EMPA 162) was obtained from Center for Testmaterials BV, P.O. Box 120, 3133 KT Vlaardingen, the Netherlands. Bistro gravy (063KC), Frij Chocolate milkshake, Heinz spaghetti (113KC), Herseys double chocolate was obtained from Warwick Equest Ltd, Unit 55, Consett Business Park, Consett, County Durham, DH8 6BN UK Results of the TOM wash test of different variants are shown in Table 3. In the result the index is 100. The performance result of the parent alpha-amylase (SEQ ID NO:7) is assigned the value of 100 and the results of the variants are compared to this value.

TABLE 2

| | Experimental conditions | |
|---|---|---|
| | European (EU) conditions | Northern America (US) conditions |
| Detergent dosage | 5.77 g/L (liquid detergent) | 0.78 g/L (liquid detergent) |
| Water hardness | 15° dH ($Ca^{2+}$:$Mg^{2+}$:$HCO_3^-$ = 4:1:7.5) | 6° dH ($Ca^{2+}$:$Mg^{2+}$:$HCO_3^-$ = 2:1:4.5) |
| Enzyme concentration in wash solution | 0.25 mg enzyme protein/L | 0.08 mg enzyme protein/L |
| Test solution volume | 500 ml | 800 ml |
| Wash time | 30 minutes | 18 minutes |
| Rotation | 120 rpm | |
| pH | as is | |
| Temperature | 15° C. | |

Detergents and test materials were as follows:

| | |
|---|---|
| Laundry liquid detergent | European (EU) conditions: Regular HDL (heavy duty liquid) as described in Example 1A below. Northern American (US) conditions: Regular HDL (heavy duty liquid) as described in Example 1B below. |
| Test material | CS-28 (Rice starch on cotton) |
| Soil ballast | Rice starch on polyester/cotton (EMPA 162), Bistro gravy (063KC), Frij Chocolate milkshake, Heinz spaghetti (113KC), Herseys double chocolate (2 swatches of each) |

The wash performance was measured as the brightness of the colour of the textile washed expressed in remission values. Remission measurements were made using a Macbeth 7000 Color Eye spectrophotometer. Each of the dry swatches was measured. As there is a risk of interference from the back-ground, the swatches were placed on top of 4 layers of fabric during the measurement of the remission. The remission was measured at 460 nm. The UV filter was not included. An average result for remission for the swatches was calculated.

Example 1

Wash Performance of Alpha-Amylases in European (EU) (Example 1A) and Northern American (Example 1B) (US) Liquid Detergent The wash performance of the tested variant and corresponding parent alpha-amylase (SEQ ID NO: 7) were tested as described above. The results are given as (performance of variant minus performance of blank) divided by (performance of parent minus performance of blank) multiplied by 100; where the blank is the performance obtained by washing at the same conditions, but in the absence of alpha-amylase.

Example 1A: European Heavy Duty Liquid Laundry Detergent Composition

| Example 1A | (wt %) |
|---|---|
| Sodium Alkylbenzene sulfonate | 11.7 |
| Citric acid | 2.27 |
| $C_{12-18}$ fatty acid | 0.82 |

-continued

| Example 1A | (wt %) |
|---|---|
| Sodium alkyl ethoxy 3 sulfate | 3.9 |
| $C_{12-18}$ alkyl 1.5-7-ethoxylate | 2.4 |
| A compound having the following general structure: bis(($C_2H_5O$)($C_2H_4O$)n)($CH_3$)—$N^+$—$C_xH_{2x}$—$N^+$—($CH_3$)—bis(($C_2H_5O$)($C_2H_4O$)n), wherein n = from 20 to 30, and x = from 3 to 8, or sulphated or sulphonated variants thereof | 0.66 |
| Random graft co-polymer[1] | 0.83 |
| Phosphonated chelant | 0.48 |
| Brightener | 0.091 |
| Hydrotrope | 0.95 |
| Minors: dyes, perfumes, enzymes, enzyme stabilizers, solvents, structurants. pH modifying agents | Balance |

[1]Random graft copolymer is a polyvinyl acetate grafted polyethylene oxide copolymer having a polyethylene oxide backbone and multiple polyvinyl acetate side chains. The molecular weight of the polyethylene oxide backbone is about 6000 and the weight ratio of the polyethylene oxide to polyvinyl acetate is about 40 to 60 and no more than 1 grafting point per 50 ethylene oxide units.

Example 1B: North American Heavy Duty Liquid Laundry Detergent Composition

| Example 1B | (wt %) |
|---|---|
| Sodium Alkyl ethoxy 1.8 sulfate | 17.29 |
| Sodium Alkylbenzene sulfonate | 7.73 |
| Branched alkyl sulfate | 3.3 |
| $C_{12-18}$ Alkyl 1.5-9ethoxylate | 1.31 |
| $C_{12}$ dimethylamine oxide | 1.03 |
| Citric acid | 0.67 |
| $C_{12-18}$ fatty acid | 1.52 |
| Sodium Borate (Borax) | 2.53 |
| Ethoxylated Polyethylenimine[2] | 1.44 |
| Phosphonated chelant | 0.34 |
| Dihydroxybenzene-3,5-disulfonic acid disodium salt hydrate | 0.19 |
| Brightener | 0.29 |
| Amphiphilic alkoxylated grease cleaningpolymer[3] | 1.93 |
| Minors: dyes, perfumes enzymes, enzyme stabilizers, solvents, structurants, pH modifying agents | Balance |

[2]Polyethylenimine (MW = 600) with 20 ethoxylate groups per —NH.
[3]Amphiphilic alkoxylated grease cleaning polymer is a polyethylenimine (MW = 600) with 24 ethoxylate groups per —NH and 16 propoxylate groups per —NH.

TABLE 3

Wash performance

| Substitutions of SEQ ID NO: 7 (numbering according to SEQ ID NO: 1) | US 20° C. AMSA | US 15° C. TOM | EU 20° C. AMSA | EU 15° C. TOM |
|---|---|---|---|---|
| N195F + V206Y + Y243F | 85 | 113 | 94 | 100 |
| E260I | 99 | 115 | 103 | 126 |
| E260K | 108 | 107 | 119 | 125 |
| W140Y + N195F + V206Y + Y243F | 104 | 108 | 110 | 104 |
| N195F + V206Y + Y243F + W284D | 120 | 107 | 78 | 126 |
| W140F + R181H | 113 | 130 | 122 | 115 |
| N195F + V206Y + E260R + G273D | 94 | 104 | 104 | 95 |
| N195F + V206Y + Y243F + E260K + G273D | 102 | 137 | 91 | 125 |
| D134E + G476E | 120 | 137 | 108 | 120 |
| K72R + N195F + V206Y + Y243F + E260H + G273V | 120 | 132 | 118 | 152 |
| N195F + V206Y + Y243F + E260N + G273V | 97 | 123 | 107 | 102 |
| W140Y + N195F + V206Y + Y243F + E260G | 107 | 149 | 119 | 111 |
| N195F + V206Y + Y243F + E260K + W284D | 136 | 209 | 107 | 116 |
| W140Y + N195F + V206Y + Y243F + E260G + W284D | 144 | 111 | 107 | 101 |
| W140Y + N195F + V206Y + Y243F + E260T + W284D | 138 | 273 | 117 | 120 |
| W189E + N195F + V206Y + Y243F | 108 | 129 | 128 | 117 |
| W140Y + N195F + V206Y + Y243F + W284D | 147 | 254 | 112 | 123 |
| N195F + V206Y + Y243F + G477R | 110 | 108 | 110 | 123 |
| N195F + V206Y + Y243F + G477M | 105 | 110 | 105 | 104 |
| W140Y + W189G + N195F + V206Y + Y243F + E260G | 124 | 132 | 103 | 113 |
| W140Y + N195F + V206Y + Y243F + E260G + G477E | 122 | 313 | 113 | 103 |
| W140Y + N195F + V206Y + Y243F + E260G + G476E | 125 | 114 | 117 | 108 |
| W140Y + N195F + V206Y + Y243F + E260G + S303G | 113 | 112 | 114 | 110 |
| W140Y + W189T + N195F + V206Y + Y243F + E260G | 119 | 112 | 123 | 111 |
| W140Y + N195F + V206Y + Y243F + E260G + G337N | 110 | 109 | 119 | 113 |
| Y100I + W140Y + N195F + V206Y + Y243F + E260G | 128 | 110 | 140 | 109 |
| G109A + W140Y + N195F + V206Y + Y243F + E260G | 115 | 245 | 129 | 116 |
| W140Y + N195F + V206Y + Y243F + E260G + W439R | 124 | 160 | 142 | 125 |
| G109A + W140Y + E194D + N195F + V206Y + Y243F + E260G | 108 | 222 | 117 | 123 |

TABLE 3-continued

Wash performance

| Substitutions of SEQ ID NO: 7 (numbering according to SEQ ID NO: 1) | US 20° C. AMSA | US 15° C. TOM | EU 20° C. AMSA | EU 15° C. TOM |
|---|---|---|---|---|
| G109A + W140Y + N195F + V206Y + Y243F + E260G + G476E | 126 | 188 | 125 | 122 |
| T51I + Y100I + G109A + W140Y + N195F + V206Y + Y243F + E260G | 113 | 175 | 128 | 110 |
| T51I + G109A + W140Y + N195F + V206Y + Y243F + E260G + W439R | 119 | 147 | 127 | 125 |
| T51I + S52Q + N54K + G109A + W140Y + N195F + V206Y + Y243F + E260G + G476E | 129 | 259 | 126 | 113 |
| W140Y + N195F + V206Y + Y243F + E260G + G304R + G476K | 124 | 179 | 135 | 125 |
| W140Y + N195F + V206Y + 243F + E260G + W284R + G477K | 132 | 309 | 144 | 124 |
| W140Y + N195F + V206Y + Y243F + E260G + W284F + G477R | 134 | 298 | 140 | 116 |
| N195F + V206Y + Y243F + E260G + W284D | 115 | 102 | 101 | 107 |
| N195F + V206Y + Y243F + S473T + G476R | 101 | 95 | 113 | 100 |
| N195F + V206Y + Y243F + G476E | 100 | 118 | 100 | 94 |

The wash performance test results clearly demonstrate that the performances of the variants are improved relative to their respective parent molecule (SEQ ID NO 7) at the tested temperatures.

Example 2

Full Scale Washing Machine Performance Evaluation of Amylase Variants in Liquid Detergent I. Preparation of the Detergent Test Compositions
In this experiment four test compositions were prepared based on liquid detergent Example 1A. A detergent base was prepared from Example 1A, containing no enzymes and finished to pH 8.2.
The following four detergent formulations were prepared:

TABLE 4

| Detergent example | |
|---|---|
| Comparative example A | Formulation as above (Ex. 1A) nil enzyme |
| Comparative example B | Formulation as above + *0.25 ppm [1]Natalase ® |
| Example C according to the invention | Formulation as above + *0.25 ppm [2]Variant 1 Amylase of this invention |
| Example D according to the invention | Formulation as above + *0.25 ppm [3]Variant 2 Amylase of this invention |

*Added as active enzyme protein
[1]Natalase ® is amylase enzyme supplied by Novozymes A/S, Bagsvaerd, Denmark as 'Natalase 200L'.
[2]Variant 1 is an amylase variant of this invention of the wild-type amylase Bacillus sp722 SEQ ID NO: 1 with the following two deletions D183* + G184* and including substitutions W140Y, N195F, V206Y, Y243F, E260G and W284D. Also ref to as SP722 + D183* + G184* + W140Y + N195F + V206Y + Y243F + E260G + W284D
[3]Variant 2 is an amylase variant of this invention of the wild-type amylase Bacillus sp722 SEQ ID NO1 with the following two deletions D183* + G184* and including substitutions W140Y, N195F, V206Y, Y243F and W284D. Also ref to as SP722 + D183* + G184* + W140Y + N195F + V206Y + Y243F + W284D.

II. Test Fabrics
Three amylase sensitive stains; CS-28 Rice Starch, PCS-28 Rice Starch and CS-29 Tapioca Starch, 5 cm×5 cm (supplied by Centre For Test materials, Netherlands) were attached to 20 cm×20 cm white knitted cotton (supplied by Warwick Equest, Durham, United Kingdom). Two amylase sensitive stains; BBQ Sauce and Frijj Chocolate Milkshake, 2.5 cm in diameter were attached to 20 cm×20 cm white knitted cotton (supplied by Warwick Equest, Durham, United Kingdom). Eight replicates (2 replicates across 4 different machines) were used for each test formulation.

TABLE 5

| | |
|---|---|
| Test materials | CS-28 Rice Starch, PCS-28 Rice Starch, CS-29 Tapioca Starch, BBQ Sauce and Frijj Chocolate Milkshake. |
| Soil ballast | Apple and pear Rice Pudding, Bisto Gravy, ASDA Gravy, Pasta Sauce, Curry Sauce, Leek & Potato Soup, Hershey's Chocolate Sauce, Chilli Con Carne, Grandma's Sunday lunch, Tomato Soup, Spaghetti Bolognese Sauce, Sweet and Sour Sauce, Brown Sauce and Carrot & Potato Babyfood (all supplied by Warwick Equest, Durham, United Kingdom). PS-28 Rice Starch, CS-128 Aged Rice Starch, CS-77 Babyfood (all supplied by Centre For Testmaterials, Netherlands). |
| Clean Ballast | 2.5 kg 50:50 mix cotton towels and sheets |

III. Test Wash Procedure
The method involves the use of Western Europe Hotpoint washing machines, model Aquarius WF541. Test formulations as described above were used to wash amylase sensitive stains with the addition of a mixed soil and clean ballast load as described above.

Washing machines containing 6 g/L of test formulation, 13 L water at 10° clark hardness, plus test fabrics & ballast were washed at 15° C. on a fast cotton wash cycle lasting 1 hour and 15 minutes. After the wash, the test fabrics were line dried indoors.

The wash process was repeated for a further 3 wash cycles.

The stain removal index (SRI) (as measured by comparing unwashed to washed L* a* b* values) was then measured in order to quantify the stain removal performance of the detergent compositions.

The performance index was also measured by calculating (performance of Example C or Example D minus the performance of comparative example A) divided by (performance of comparative example B minus the performance of comparative example A) multiplied by 100.

IV. Comparison of the Samples.

TABLE 6

Average SRI across 5 stains (8 replicates of each stain)

| Example | Average SRI (%) (associated LSD) | Average SRI versus A | Average SRI versus B |
|---|---|---|---|
| Comparative example A | 44.2 (3.1) | — | — |
| Comparative example B | 62.1 (3.1) | 17.2 | — |
| Example C According to the invention | 72.1 (3.1) | 27.5 | 10.3 |
| Example D According to the invention | 70.9 (3.1) | 26.5 | 9.3 |

TABLE 7

Performance Index for CS-29 Tapioca Starch (8 replicates)

| Example | Performance Index |
|---|---|
| Comparative example A | — |
| Comparative example B | 100 |
| Example C According to the invention | 157 |
| Example D According to the invention | 150 |

By comparing the samples washed with the composition of example A (nil enzyme present) with example B (containing Natalase), C and D (containing variant 1 and 2 respectively), it is apparent that the stain removal performance is improved by the addition of an amylase enzyme. By comparing the samples washed with the composition of example B (containing Natalase) with examples C and D (containing variant 1 and 2 respectively) according to example A as the reference (nil enzyme), it is apparent that both variants 1 and 2 of the invention are able to achieve significantly higher levels of stain removal than Natalase).

Example 3

Full Scale Washing Machine Performance Evaluation of Amylase Variants in Liquid Detergent I. Preparation of the Detergent Test Compositions In this experiment four test compositions were prepared based on liquid detergent example 1B above. A detergent base was prepared from example 1B, containing no enzymes and finished to pH 8.2.

The following four formulations were prepared:

TABLE 8

| Example | |
|---|---|
| Comparative example A | Formulation as above (Ex. 1B) nil enzyme |
| Comparative example B | Formulation as above + *0.1 ppm [1]Natalase ® |
| Example C according to the invention | Formulation as above + *0.1 ppm [4]Variant 3 Amylase of this invention |
| Example D according to the invention | Formulation as above + *0.1 ppm [5]Variant 4 Amylase of this invention |

*Added as active enzyme protein

[1]Natalase ® is supplied by Novozymes A/S, Bagsvaerd, Denmark as 'Natalase 200L'.

[4]Variant 3 is an amylase variant of this invention of the wild-type amylase Bacillus sp722 SEQ ID NO1 with the following two deletions D183* + G184* and including substitutions W140Y, N195F, V206Y, Y243F, E260G and G477E. Also ref to as SP722 + D183* + G184* + W140Y + N195F + V206Y + Y243F + E260G + G477E

[5]Variant 4 is an amylase variant of this invention of the wild-type amylase Bacillus sp722 SEQ ID NO: 1 with the following two deletions D183* + G184* and including substitutions G109A, W140Y, N195F, V206Y, Y243F and E260G. Also ref to as SP722 + D183* + G184* + G109A + W140Y + N195F + V206Y + Y243F + E260G.

II. Test Fabrics

Three amylase sensitive stains; PCS-28 Rice Starch, PS-28 Rice Starch and CS-26 Corn Starch, 5 cm×5 cm (supplied by Centre For Test materials, Netherlands) were attached to 20 cm×20 cm white knitted cotton (supplied by Warwick Equest, Durham, United Kingdom). Two amylase sensitive stains; BBQ Sauce and Chocolate Pudding Babyfood, 2.5 cm in diameter were attached to 20 cm×20 cm white knitted cotton (supplied by Warwick Equest, Durham, United Kingdom). Eight replicates (2 replicates across 4 different machines) were used for each test formulation.

TABLE 9

| | |
|---|---|
| Test materials | PCS-28 Rice Starch, PS-28 Rice Starch, CS-26 Corn Starch, BBQ Sauce and Chocolate Pudding Babyfood. |
| Soil ballast | Bisto Gravy, Hershey's Chocolate Sauce, Tomato Soup, Chilli Con Carne, Leek & Potato Soup, Spaghetti Bolognese Sauce (all supplied by Warwick Equest, Durham, United Kingdom). Grass, Double Chocolate Syrup, US Clay, Make Up, Wine, Tea and Spaghetti (all supplied by APD, Ohio, United States). CS-28 Rice Starch, CS-128 Aged Rice Starch, CS-29 Tapioca Starch (all supplied by Centre For Testmaterials, Netherlands). |
| Clean Ballast | 6 x cotton T shirts 6 x cotton pillowcases 6 x hand towels |

III. Test Wash Procedure

The method involves the use of a North American Kenmore washing machine model 600 series. Test formulations as described above were used to wash amylase sensitive stains with the addition of a mixed soil and clean ballast load as described above.

Washing machines containing 0.78 g/L test formulation, 64 L water 6° clark water hardness, plus test fabrics & ballast were washed at 15° C. on a 12 minute superwash with one rinse. After the wash, the test fabrics were line dried indoors.

The wash process was repeated for a further 3 wash cycles.

The stain removal index (as measured by comparing unwashed to washed L* a* b* values) was then measured in order to quantify the stain removal performance of the detergent compositions.

The performance index was also measured by calculating (performance of Example C or Example D minus the performance of comparative example A) divided by (performance of comparative example B minus the performance of comparative example A) multiplied by 100.

IV. Comparison of the Samples.

TABLE 10

Average SRI across 5 stains (8 replicates of each stain)

| Example | Average SRI (%) (associated LSD) | Average SRI versus A | Average SRI versus B |
|---|---|---|---|
| Comparative Example A | 36.4 (4.3) | — | — |
| Comparative Example B | 44.9 (4.3) | 8.5 | — |
| Example C According to the invention | 56.5 (4.3) | 20.1 | 11.6 |
| Example D According to the invention | 55.0 (4.3) | 18.5 | 10 |

TABLE 11

Performance Index for CS-26 Corn Starch (8 replicates)

| Example | Performance Index |
|---|---|
| Comparative Example A | — |
| Comparative Example B | 100 |
| Example C According to the invention | 221 |
| Example D According to the invention | 238 |

By comparing the samples washed with the composition of example A (nil enzyme present) with example B (containing Natalase), C and D (containing variant 3 and 4 respectively), it is apparent that the stain removal performance is improved by the addition of an amylase enzyme. By comparing the samples washed with the composition of example B (containing Natalase) with examples C and D (containing variant 3 and 4 respectively) according to example A as the reference (nil enzyme), it is apparent that both variants 3 and 4 of the invention are able to achieve significantly higher levels of stain removal than Natalase®.

Example 4

Full Scale Washing Machine Performance Evaluation of Amylase Variants in Liquid Detergent I. Preparation of the Detergent Test Compositions In this experiment four test compositions were prepared based on liquid detergent formulation 4A below. A detergent base was prepared from formulation 4A, containing no enzymes and finished to pH 8.2.

TABLE 12

Formulation 4A: Heavy Duty Liquid laundry detergent composition

| Formulation 4A | (wt %) |
|---|---|
| Sodium Alkylbenzene sulfonate | 10.2 |
| Citric acid | 3.14 |
| $C_{12-18}$ fatty acid | 2.59 |
| Sodium Alkyl ethoxy 3 sulfate | 1.17 |
| $C_{12-18}$ Alkyl 1.5-7-ethoxylate | 6.32 |
| A compound having the following general structure: bis$((C_2H_5O)(C_2H_4O)n)(CH_3)$—$N^+$—$C_xH_{2x}$—$N^+$—$(CH_3)$—bis$((C_2H_5O)(C_2H_4O)n)$, wherein n = from 20 to 30, and x = from 3 to 8, or sulphated or sulphonated variants thereof | 0.63 |
| Random graft co-polymer[1] | 1.07 |
| Phosphonated chelant | 0.41 |
| Brightener | 0.09 |
| Hydrotrope | 0.93 |
| Minors: dyes, perfumes enzymes, enzyme stabilizers, solvents, structurants, pH modifying agents | Balance |

[1]Random graft copolymer is a polyvinyl acetate grafted polyethylene oxide copolymer having a polyethylene oxide backbone and multiple polyvinyl acetate side chains. The molecular weight of the polyethylene oxide backbone is about 6000 and the weight ratio of the polyethylene oxide to polyvinyl acetate is about 40 to 60 and no more than 1 grafting point per 50 ethylene oxide units.

The following seven detergent formulations were prepared:

TABLE 13

| Detergent formulation 4A | |
|---|---|
| Comparative example A | Formulation 4A - Nil enzyme |
| Comparative example B | Addition of *0.23 ppm [1]Natalase ® |
| Example C according to the invention | Addition of *0.23 ppm [2]Variant 5 Amylase of this invention |
| Example D according to the invention | Addition of *0.23 ppm [3]Variant 6 Amylase of this invention |
| Example E according to the invention | Addition of *0.23 ppm [4]Variant 7 Amylase of this invention |
| Example F according to the invention | Addition of *0.23 ppm [5]Variant 8 Amylase of this invention |
| Example G according to the invention | Addition of *0.23 ppm [6]Variant 9 Amylase of this invention |

*Added as active enzyme protein
[1]Natalase ® is amylase enzyme supplied by Novozymes A/S, Bagsvaerd, Denmark as 'Natalase 200L'.
[2]Variant 5 is an amylase variant of this invention of the wild-type amylase Bacillus sp722 SEQ ID NO1 with the following two deletions D183* + G184* and including substitutions G109A, W140Y, N195F, V206Y, Y243F, E260G and G476E. Also referred to as SP722 + D183* + G184* + G109A + W140Y + N195F + V206Y + Y243F + E260G + G476E.
[3]Variant 6 is an amylase variant of this invention of the wild-type amylase Bacillus sp722 SEQ ID NO1 with the following two deletions D183* + G184* and including substitutions T51I, G109A, W140Y, N195F, V206Y, Y243F, E260G and W439R. Also referred to as SP722 + D183* + G184* + T51I + G109A + W140Y + N195F + V206Y + Y243F + E260G + W439R.
[4]Variant 7 is an amylase variant of this invention of the wild-type amylase Bacillus sp722 SEQ ID NO1 with the following two deletions D183* + G184* and including substitutions T51I, S52Q, N54K, G109A, W140Y, N195F, V206Y, Y243F, E260G and G476E. Also referred to as SP722 + D183* + G184* + T51I + S52Q + N54K + G109A + W140Y + N195F + V206Y + Y243F + E260G + G476E.
[5]Variant 8 is an amylase variant of this invention of the wild-type amylase Bacillus sp722 SEQ ID NO1 with the following two deletions D183* + G184* and including substitutions W140Y, N195F, V206Y, Y243F, E260G, G304R and G476K. Also referred to as SP722 + D183* + G184* + W140Y + N195F + V206Y + Y243F + E260G + G304R + G476K.
[6]Variant 9 is an amylase variant of this invention of the wild-type amylase Bacillus sp722 SEQ ID NO1 with the following two deletions D183* + G184* and including substitutions W140Y, N195F, V206Y, Y243F, E260G, W284R and G477K. Also referred to as SP722 + D183* + G184* + W140Y + N195F + V206Y + Y243F + E260G + W284R + G477K.

II. Test Fabrics

Three amylase sensitive stains; PCS-28 Rice Starch, CS-128 Aged Rice Starch and CS-26 Corn Starch, 5 cm×5 cm (supplied by Centre For Test materials, Netherlands) were attached to 20 cm×20 cm white knitted cotton (supplied by Warwick Equest, Durham, United Kingdom). Two amylase sensitive stains; Chilli Con Carne and Heinz Spaghetti, 2.5 cm in diameter were attached to 20 cm×20 cm white knitted cotton (supplied by Warwick Equest, Durham, United Kingdom). Eight replicates (2 replicates across 4 different machines) were used for each test formulation.

TABLE 14

| Test materials | PCS-28 Rice Starch, CS-128 Aged Rice Starch, CS-26 Corn Starch, Chilli Con Carne and Heinz Spaghetti. |
|---|---|
| Soil ballast | Apple and Pear Rice Pudding, Grandma's Sunday Lunch, Tomato Soup, Spaghetti Bolognese Sauce, Sweet and Sour Sauce, Carrot and Potato Babyfood, Bisto Gravy, ASDA Gravy, ASDA Pasta Sauce, BBQ Sauce, Curry Sauce, |

TABLE 14-continued

| | |
|---|---|
| | Frijj Chocolate Milkshake, Leek and Potato Soup, Hershey's Chocolate Syrup (all supplied by Warwick Equest, Durham, United Kingdom). CS-28 Rice Starch, PS-28 Rice Starch, CS-29 Tapioca Starch (all supplied by Centre For Testmaterials, Netherlands). |
| Clean Ballast | 2.5 kg 50:50 mix cotton towels and sheets |

III. Test Wash Procedure

The method involves the use of Western Europe Hotpoint washing machines, model Aquarius WF541. Test formulations as described above were used to wash amylase sensitive stains with the addition of a mixed soil and clean ballast load as described above.

Washing machines containing 6 g/L of test formulation, 13 L water at 10° clark hardness, plus test fabrics & ballast were washed at 15° C. on a fast cotton wash cycle lasting 1 hour and 15 minutes. After the wash, the test fabrics were line dried indoors.

The wash process was repeated for a further 3 wash cycles.

The stain removal index (SRI) (as measured by comparing unwashed to washed $L^*$ $a^*$ $b^*$ values) was then measured in order to quantify the stain removal performance of the detergent compositions.

The performance index was also measured by calculating (performance of Example C, D, E, F or G minus the performance of comparative example A) divided by (performance of comparative example B minus the performance of comparative example A) multiplied by 100.

IV. Comparison of the Samples.

TABLE 15

Average SRI across 5 stains (8 replicates of each stain)

| Example | Average SRI (%) (associated LSD) | Average SRI versus A | Average SRI versus B |
|---|---|---|---|
| Comparative example A | 33.2 (3.7) | — | — |
| Comparative example B | 55.2 (3.7) | 22.0 | — |
| Example C According to the invention | 66.1 (3.7) | 32.9 | 10.9 |
| Example D According to the invention | 64.0 (3.7) | 30.8 | 8.8 |
| Example E According to the invention | 66.8 (3.7) | 33.6 | 11.6 |
| Example F According to the invention | 64.6 (3.7) | 31.4 | 9.4 |
| Example G According to the invention | 67.8 (3.7) | 34.6 | 12.6 |

TABLE 16

Performance Index for Chilli Con Carne (8 replicates)

| Example | Performance Index |
|---|---|
| Comparative example A | — |
| Comparative example B | 100 |
| Example C According to the invention | 169 |
| Example D According to the invention | 145 |
| Example E According to the invention | 181 |
| Example F According to the invention | 178 |
| Example G According to the invention | 188 |

By comparing the samples washed with the composition of example A (nil enzyme present) with example B (containing Natalase), C, D, E, F & G (containing variants 5, 6, 7, 8 & 9 respectively), it is apparent that the stain removal performance is improved by the addition of an amylase enzyme.

By comparing the samples washed with the composition of example B (containing Natalase) with examples C, D, E, F & G (containing variants 5, 6, 7, 8 & 9 respectively) according to example A as the reference (nil enzyme), it is apparent that variants 5, 6, 7, 8 & 9 of the invention are able to achieve significantly higher levels of stain removal than Natalase®.

Example 5

Full Scale Washing Machine Performance Evaluation of Amylase Variants in Liquid Detergent

I. Preparation of the Detergent Test Compositions

In this experiment four test compositions were prepared based on liquid detergent formulation 5A. A detergent base was prepared from formulation 5A, containing no enzymes and finished to pH 8.2.

TABLE 17

Formulation 5A Heavy Duty Liquid laundry detergent composition

| Formulation 5A | (wt %) |
|---|---|
| Sodium Alkyl ethoxy 1.8 sulfate | 14.81 |
| Sodium Alkylbenzene sulfonate | 3.53 |
| Branched alkyl sulfate | 2.44 |
| $C_{12-18}$ Alkyl - 1.5-9-ethoxylate | 0.88 |
| $C_{12}$ dimethylamine oxide | 0.56 |
| Citric acid | 2.05 |
| $C_{12-18}$ fatty acid | 1.48 |
| Ethoxylated Polyethylenimine [2] | 1.51 |
| Phosphonated chelant | 0.53 |
| Brightener | 0.19 |
| Amphiphilic alkoxylated polymer [3] | 1.25 |
| Minors: dyes, perfumes enzymes, enzyme stabilizers, solvents, structurants, pH modifying agents | Balance |

[2] Polyethylenimine (MW = 600) with 20 ethoxylate groups per —NH.
[3] Amphiphilic alkoxylated polymer is a polyethylenimine (MW 600), prepared from a polymer that is derivatised to contain 24 ethoxylate groups per —NH and 16 Propoxylate groups per —NH.

TABLE 18

| Formulation 5A | |
|---|---|
| Comparative example A | Formulation 5A - Nil enzyme |
| Comparative example B | Addition of *0.1 ppm [1]Natalase ® |
| Example C according to the invention | Addition of *0.1 ppm [2]Variant 7 Amylase of this invention |
| Example D according to the invention | Addition of *0.1 ppm [3]Variant 8 Amylase of this invention |

TABLE 18-continued

| Formulation 5A | |
| --- | --- |
| Example E according to the invention | Addition of *0.1 ppm [4]Variant 9 Amylase of this invention |
| Example F according to the invention | Addition of *0.1 ppm [5]Variant 10 Amylase of this invention |

The following six formulations were prepared:
*Added as active enzyme protein
[1]Natalase ® is supplied by Novozymes A/S, Bagsvaerd, Denmark as 'Natalase 200L'.
[2]Variant 7 is an amylase variant of this invention of the wild-type amylase *Bacillus* sp722 SEQ ID NO1 with the following two deletions D183* + G184* and including substitutions T51I, S52Q, N54K, G109A, W140Y, N195F, V206Y, Y243F, E260G and G476E. Also referred to as SP722 + D183* + G184* + T51I + S52Q + N54K + G109A + W140Y + N195F + V206Y + Y243F + E260G + G476E.
[3]Variant 8 is an amylase variant of this invention of the wild-type amylase *Bacillus* sp722 SEQ ID NO1 with the following two deletions D183* + G184* and including substitutions W140Y, N195F, V206Y, Y243F, E260G, G304R and G476K. Also referred to as SP722 + D183* + G184* + W140Y + N195F + V206Y + Y243F + E260G + G304R + G476K.
[4]Variant 9 is an amylase variant of this invention of the wild-type amylase *Bacillus* sp722 SEQ ID NO1 with the following two deletions D183* + G184* and including substitutions W140Y, N195F, V206Y, Y243F, E260G, W284R and G477K. Also referred to as SP722 + D183* + G184* + W140Y + N195F + V206Y + Y243F + E260G + W284R + G477K.
[5]Variant 10 is an amylase variant of this invention of the wild-type amylase *Bacillus* sp722 SEQ ID NO1 with the following two deletions D183* + G184* and including substitutions W140Y, N195F, V206Y, Y243F, E260G, W284F and G477R. Also referred to as SP722 + D183* + G184* + W140Y + N195F + V206Y + Y243F + E260G + W284F + G477R.

II. Test Fabrics

Three amylase sensitive stains; PCS-28 Rice Starch, PS-28 Rice Starch and CS-29 Tapioca Starch, 5 cm×5 cm (supplied by Centre For Test materials, Netherlands) were attached to 20 cm×20 cm white knitted cotton (supplied by Warwick Equest, Durham, United Kingdom). One amylase sensitive stain; Heinz Spaghetti, 2.5 cm in diameter was attached to 20 cm×20 cm white knitted cotton (supplied by Warwick Equest, Durham, United Kingdom). One amylase sensitive stain; Gravy, 2.5 cm in diameter was attached to 25 cm×24 cm white knitted cotton (supplied by Accurate Product Development, Fairfield, Ohio, USA). Eight replicates (2 replicates across 4 different machines) were used for each test formulation.

TABLE 19

| Test materials | PCS-28 Rice Starch, PS-28 Rice Starch, CS-29 Tapioca Starch, Heinz Spaghetti and Gravy. |
| --- | --- |
| Soil ballast | BBQ Sauce, Bisto Gravy, Chocolate Pudding Babyfood, Hershey's Chocolate Sauce, Tomato Soup, Chilli Con Carne, Spaghetti Bolognese Sauce (all supplied by Warwick Equest, Durham, United Kingdom). Grape Juice, Mustard, Coffee, Blueberry, BBQ Sauce, Blood, Grass, Burnt Butter, Bacon Grease, Double Chocolate Syrup, US Clay, Make Up, Wine, Tea and Spaghetti (all supplied by APD, Fairfield, Ohio, United States). CS-28 Rice Starch, CS-128 Aged Rice Starch, CS-26 Corn Starch (all supplied by Centre For Testmaterials, Netherlands). |
| Clean Ballast | 6 × cotton T shirts, 6 × cotton pillowcases, 6 × hand towels |

III. Test Wash Procedure

The method involves the use of a North American Kenmore washing machine model 600 series. Test formulations as described above were used to wash amylase sensitive stains with the addition of a mixed soil and clean ballast load as described above.

Washing machines containing 0.78 g/L test formulation, 64 L water 6° clark water hardness, plus test fabrics & ballast were washed at 15° C. on a 12 minute superwash with one rinse. After the wash, the test fabrics were line dried indoors. The wash process was repeated for a further 3 wash cycles.

The stain removal index (as measured by comparing unwashed to washed L* a* b* values) was then measured in order to quantify the stain removal performance of the detergent compositions.

The performance index was also measured by calculating (performance of Example C, D, E or F minus the performance of comparative example A) divided by (performance of comparative example B minus the performance of comparative example A) multiplied by 100.

IV. Comparison of the Samples.

TABLE 20

Average SRI across 5 stains (8 replicates of each stain)

| Example | Average SRI (%) (associated LSD) | Average SRI versus A | Average SRI versus B |
| --- | --- | --- | --- |
| Comparative Example A | 39.5 (4.8) | — | — |
| Comparative Example B | 51.4 (4.8) | 11.9 | — |
| Example C According to the invention | 69.4 (4.8) | 29.9 | 18.0 |
| Example D According to the invention | 64.7 (4.8) | 25.2 | 13.3 |
| Example E According to the invention | 71.3 (4.8) | 31.8 | 19.9 |
| Example F According to the invention | 69.2 (4.8) | 29.7 | 17.8 |

TABLE 21

Performance Index for Heinz Spaghetti (8 replicates)

| Example | Performance Index |
| --- | --- |
| Comparative Example A | — |
| Comparative Example B | 100 |
| Example C According to the invention | 266 |
| Example D According to the invention | 256 |
| Example E According to the invention | 284 |
| Example F According to the invention | 416 |

By comparing the samples washed with the composition of example A (nil enzyme present) with example B (containing Natalase), C, D, E and F (containing variant 7, 8, 9 and 10 respectively), it is apparent that the stain removal performance is improved by the addition of an amylase enzyme.

By comparing the samples washed with the composition of example B (containing Natalase) with examples C, D, E and F (containing variant 7, 8, 9 and 10 respectively) according to comparative example A as the reference (nil enzyme), it is apparent that variants 7, 8, 9 and 10 of the invention are able to achieve significantly higher levels of stain removal than Natalase®.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

The invention claimed is:

1. An isolated variant of a parent alpha-amylase, comprising at least three substitutions at positions corresponding to positions 134, 206 and 260 of the polypeptide of SEQ ID NO: 1, wherein the variant has at least 90% but less than 100% sequence identity with the polypeptide of any of SEQ ID NOs 1, 2, 3, 4, 5, 6, 7, 10, 11 or 12, and wherein the variant has alpha-amylase activity.

2. The variant according to claim 1, which comprises a substitution at three positions selected from the group consisting of G304, W140, W189, D134, E260, F262, W284, W347, W439, W469, G476, and G477.

3. The variant according to claim 1, which comprises a substitution at four positions selected from the group consisting of G304, W140, W189, D134, E260, F262, W284, W347, W439, W469, G476, and G477.

4. The variant according to claim 1, which comprises a substitution at two, three or four positions selected from the group consisting of G304, W140, E260 and G476.

5. The variant of claim 1, which comprises two or more (several) substitutions selected from the group consisting of G304R, W140YF, W189EGT, D134E, E260GHIKNRTY, W284DFR, W439RG, W469EK, G477EKMR.

6. The variant according to claim 1, which comprises substitutions at two, three or four positions selected from the group consisting of G304R, W140YF, E260GHIKNRTY and G476EK.

7. The variant according to claim 6, wherein the substitutions at the two, three or four positions are selected from the group consisting of G304R, W140Y, E260G and G476K.

8. The variant of claim 1, further comprising one or more substitutions selected from the group consisting of N195F, V206Y, Y243F, G109A, G273DV, G337N, K72R, R181H, S303G and Y100I.

9. The variant according to claim 1, wherein the number of alterations is 2-20.

10. The variant according to claim 1, which has at least 95% identity, at least 96%, at least 97%, at least 98%, at least 99%, but less than 100%, sequence identity with the mature polypeptide of any of SEQ ID NOs 1, 2, 3, 4, 5, 6, 7, 8, 9, 10, 11 or 12.

11. The variant according to claim 1, which comprises substitutions in the positions, corresponding to the positions of the polypeptide of SEQ ID NO: 1, selected from the group consisting of:

W140Y+N195F+V206Y+Y243F+E260G+G477E,
W140Y+N195F+V206Y+Y243F+E260T+W284D,
W140Y+N195F+V206Y+Y243F+W284D,
G109A+W140Y+N195F+V206Y+Y243F+E260G,
W140Y+N195F+V206Y+Y243F+E260G,
N195F+V206Y+Y243F+E260K+W284D,
D134E+G476E,
W140Y+N195F+V206Y+Y243F+E260G+G476E,
W140Y+W189G+N195F+V206Y+Y243F+E260G,
W140Y+N195F+V206Y+Y243F+E260G+S303G,
W140Y+W189T+N195F+V206Y+Y243F+E260G,
W140Y+N195F+V206Y+Y243F+E260G+W284D,
Y100I+W140Y+N195F+V206Y+Y243F+E260G,
W140Y+N195F+V206Y+Y243F+E260G+G337N,
W140Y+N195F+V206Y+Y243F+E260G+W439R
G109A+W140Y+E194D+N195F+V206Y+Y243F+E260G
G109A+W140Y+N195F+V206Y+Y243F+E260G+G476E
T51I+Y100I+G109A+W140Y+N195F+V206Y+Y243F+E260G
T51I+G109A+W140Y+N195F+V206Y+Y243F+E260G+W439R

T51I+S52Q+N54K+G109A+W140Y+N195F+V206Y+
  Y243F+E260G+G476E
W140Y+N195F+V206Y+Y243F+E260G+G304R+
  G476K
W140Y+N195F+V206Y+Y243F+E260G+W284R+
  G477K
W140Y+N195F+V206Y+Y243F+E260G+W284F+
  G477R, and
N195F+V206Y+Y243F+E260G+W284D.

12. The variant according to claim 1, which consists of substitutions in the positions, corresponding to the positions of the polypeptide of SEQ ID NO: 1, selected from the group consisting of:
  W140Y+N195F+V206Y+Y243F+E260G+G477E,
  W140Y+N195F+V206Y+Y243F+E260T+W284D,
  W140Y+N195F+V206Y+Y243F+W284D,
  G109A+W140Y+N195F+V206Y+Y243F+E260G,
  W140Y+N195F+V206Y+Y243F+E260G,
  N195F+V206Y+Y243F+E260K+W284D,
  D134E+G476E,
  W140Y+N195F+V206Y+Y243F+E260G+G476E,
  W140Y+W189G+N195F+V206Y+Y243F+E260G,
  W140Y+N195F+V206Y+Y243F+E260G+S303G,
  W140Y+W189T+N195F+V206Y+Y243F+E260G,
  W140Y+N195F+V206Y+Y243F+E260G+W284D,
  Y100I+W140Y+N195F+V206Y+Y243F+E260G,
  W140Y+N195F+V206Y+Y243F+E260G+G337N,
  W140Y+N195F+V206Y+Y243F+E260G+W439R
  G109A+W140Y+E194D+N195F+V206Y+Y243F+
    E260G
  G109A+W140Y+N195F+V206Y+Y243F+E260G+
    G476E
  T51I+Y100I+G109A+W140Y+N195F+V206Y+Y243F+
    E260G
  T51I+G109A+W140Y+N195F+V206Y+Y243F+
    E260G+W439R
  T51I+S52Q+N54K+G109A+W140Y+N195F+V206Y+
    Y243F+E260G+G476E
  W140Y+N195F+V206Y+Y243F+E260G+G304R+
    G476K
  W140Y+N195F+V206Y+Y243F+E260G+W284R+
    G477K
  W140Y+N195F+V206Y+Y243F+E260G+W284F+
    G477R, and
  N195F+V206Y+Y243F+E260G+W284D.

13. The variant according to claim 1, which further comprises deletions at positions corresponding to positions G182*+D183* or D183*+G184* of SEQ ID NO:1.

14. The variant according to claim 1, which comprises alterations in the positions, corresponding to the positions of the polypeptide of SEQ ID NO: 1, selected from the group consisting of:
  D183*+G184*+W140Y+N195F+V206Y+Y243F+
    E260G+G477E,
  D183*+G184*+W140Y+N195F+V206Y+Y243F+
    E260T+W284D,
  D183*+G184*+W140Y+N195F+V206Y+Y243F+
    W284D,
  D183*+G184*+G109A+W140Y+N195F+V206Y+
    Y243F+E260G,
  D183*+G184*+W140Y+N195F+V206Y+Y243F+
    E260G,
  D183*+G184*+N195F+V206Y+Y243F+E260K+
    W284D,
  D183*+G184*+D134E+G476E,
  D183*+G184*+W140Y+N195F+V206Y+Y243F+
    E260G+G476E,
  D183*+G184*+W140Y+W189G+N195F+V206Y+
    Y243F+E260G,
  D183*+G184*+W140Y+N195F+V206Y+Y243F+
    E260G+S303G,
  D183*+G184*+W140Y+W189T+N195F+V206Y+
    Y243F+E260G,
  D183*+G184*+W140Y+N195F+V206Y+Y243F+
    E260G+W284D,
  D183*+G184*+Y100I+W140Y+N195F+V206Y+
    Y243F+E260G,
  D183*+G184*+W140Y+N195F+V206Y+Y243F+
    E260G+G337N,
  D183*+G184*+W140Y+N195F+V206Y+Y243F+
    E260G+W439R,
  D183*+G184*+G109A+W140Y+E194D+N195F+
    V206Y+Y243F+E260G
  D183*+G184*+G109A+W140Y+N195F+V206Y+
    Y243F+E260G+G476E
  D183*+G184*+T51I+Y100I+G109A+W140Y+N195F+
    V206Y+Y243F+E260G
  D183*+G184*+T51I+G109A+W140Y+N195F+
    V206Y+Y243F+E260G+W439R
  D183*+G184*+T51I+S52Q+N54K+G109A+W140Y+
    N195F+V206Y+Y243F+E260G+G476E
  D183*+G184*+W140Y+N195F+V206Y+Y243F+
    E260G+G304R+G476K
  D183*+G184*+W140Y+N195F+V206Y+Y243F+
    E260G+W284R+G477K
  D183*+G184*+W140Y+N195F+V206Y+Y243F+
    E260G+W284F+G477R, and
  D183*+G184*+N195F+V206Y+Y243F+E260G+
    W284D.

15. The variant according to claim 1, which consists of alterations in the positions, corresponding to the positions of the polypeptide of SEQ ID NO: 1, selected from the group consisting of:
  D183*+G184*+W140Y+N195F+V206Y+Y243F+
    E260G+G477E,
  D183*+G184*+W140Y+N195F+V206Y+Y243F+
    E260T+W284D,
  D183*+G184*+W140Y+N195F+V206Y+Y243F+
    W284D,
  D183*+G184*+G109A+W140Y+N195F+V206Y+
    Y243F+E260G,
  D183*+G184*+W140Y+N195F+V206Y+Y243F+
    E260G,
  D183*+G184*+N195F+V206Y+Y243F+E260K+
    W284D,
  D183*+G184*+D134E+G476E,
  D183*+G184*+W140Y+N195F+V206Y+Y243F+
    E260G+G476E,
  D183*+G184*+W140Y+W189G+N195F+V206Y+
    Y243F+E260G,
  D183*+G184*+W140Y+N195F+V206Y+Y243F+
    E260G+S303G,
  D183*+G184*+W140Y+W189T+N195F+V206Y+
    Y243F+E260G,
  D183*+G184*+W140Y+N195F+V206Y+Y243F+
    E260G+W284D,
  D183*+G184*+Y100I+W140Y+N195F+V206Y+
    Y243F+E260G,
  D183*+G184*+W140Y+N195F+V206Y+Y243F+
    E260G+G337N,
  D183*+G184*+W140Y+N195F+V206Y+Y243F+
    E260G+W439R
  D183*+G184*+G109A+W140Y+E194D+N195F+
    V206Y+Y243F+E260G D183*+G184*+G109A+W140Y+N195F+V206Y+
  Y243F+E260G+G476E
D183*+G184*+T51I+Y100I+G109A+W140Y+N195F+
  V206Y+Y243F+E260G
D183*+G184*+T51I+G109A+W140Y+N195F+
  V206Y+Y243F+E260G+W439R
D183*+G184*+T51I+S52Q+N54K+G109A+W140Y+
  N195F+V206Y+Y243F+E260G+G476E
D183*+G184*+W140Y+N195F+V206Y+Y243F+
  E260G+G304R+G476K
D183*+G184*+W140Y+N195F+V206Y+Y243F+
  E260G+W284R+G477K
D183*+G184*+W140Y+N195F+V206Y+Y243F+
  E260G+W284F+G477R, and
D183*+G184*+N195F+V206Y+Y243F+E260G+
  W284D.

16. An isolated polynucleotide encoding the variant of claim 1.

17. A nucleic acid construct comprising the polynucleotide of claim 16.

18. An expression vector comprising the polynucleotide of claim 16.

19. A host cell comprising the polynucleotide of claim 16.

20. A method of producing a variant of a parent alpha-amylase, comprising cultivating the host cell of claim 19 under conditions suitable for the expression of the variant; and recovering the variant.

21. A method for obtaining a variant of a parent alpha-amylase, comprising introducing into the parent alpha-amylase comprising at least three substitutions at positions corresponding to positions 134, 206 and 260 of the polypeptide of SEQ ID NO: 1, wherein the variant has at least 90% but less than 100% sequence identity with the polypeptide of any of SEQ ID NOs 1, 2, 3, 4, 5, 6, 7, 10, 11 or 12, and wherein the variant has alpha-amylase activity; and recovering the variant.

* * * * *

SEQUENCE LISTING

<160> NUMBER OF SEQ ID NOS: 12

<210> SEQ ID NO 1
<211> LENGTH: 485
<212> TYPE: PRT
<213> ORGANISM: Bacillus sp.

<400> SEQUENCE: 1

```
His His Asn Gly Thr Asn Gly Thr Met Met Gln Tyr Phe Glu Trp His
1               5                   10                  15

Leu Pro Asn Asp Gly Asn His Trp Asn Arg Leu Arg Asp Asp Ala Ser
            20                  25                  30

Asn Leu Arg Asn Arg Gly Ile Thr Ala Ile Trp Ile Pro Pro Ala Trp
        35                  40                  45

Lys Gly Thr Ser Gln Asn Asp Val Gly Tyr Gly Ala Tyr Asp Leu Tyr
50                  55                  60

Asp Leu Gly Glu Phe Asn Gln Lys Gly Thr Val Arg Thr Lys Tyr Gly
65                  70                  75                  80

Thr Arg Ser Gln Leu Glu Ser Ala Ile His Ala Leu Lys Asn Asn Gly
                85                  90                  95

Val Gln Val Tyr Gly Asp Val Val Met Asn His Lys Gly Gly Ala Asp
            100                 105                 110

Ala Thr Glu Asn Val Leu Ala Val Glu Val Asn Pro Asn Asn Arg Asn
        115                 120                 125

Gln Glu Ile Ser Gly Asp Tyr Thr Ile Glu Ala Trp Thr Lys Phe Asp
    130                 135                 140

Phe Pro Gly Arg Gly Asn Thr Tyr Ser Asp Phe Lys Trp Arg Trp Tyr
145                 150                 155                 160

His Phe Asp Gly Val Asp Trp Asp Gln Ser Arg Gln Phe Gln Asn Arg
                165                 170                 175

Ile Tyr Lys Phe Arg Gly Asp Gly Lys Ala Trp Asp Trp Glu Val Asp
            180                 185                 190

Ser Glu Asn Gly Asn Tyr Asp Tyr Leu Met Tyr Ala Asp Val Asp Met
        195                 200                 205

Asp His Pro Glu Val Val Asn Glu Leu Arg Arg Trp Gly Glu Trp Tyr
    210                 215                 220

Thr Asn Thr Leu Asn Leu Asp Gly Phe Arg Ile Asp Ala Val Lys His
225                 230                 235                 240

Ile Lys Tyr Ser Phe Thr Arg Asp Trp Leu Thr His Val Arg Asn Ala
                245                 250                 255

Thr Gly Lys Glu Met Phe Ala Val Ala Glu Phe Trp Lys Asn Asp Leu
            260                 265                 270

Gly Ala Leu Glu Asn Tyr Leu Asn Lys Thr Asn Trp Asn His Ser Val
        275                 280                 285

Phe Asp Val Pro Leu His Tyr Asn Leu Tyr Asn Ala Ser Asn Ser Gly
    290                 295                 300

Gly Asn Tyr Asp Met Ala Lys Leu Leu Asn Gly Thr Val Val Gln Lys
305                 310                 315                 320

His Pro Met His Ala Val Thr Phe Val Asp Asn His Asp Ser Gln Pro
                325                 330                 335

Gly Glu Ser Leu Glu Ser Phe Val Gln Glu Trp Phe Lys Pro Leu Ala
            340                 345                 350

Tyr Ala Leu Ile Leu Thr Arg Glu Gln Gly Tyr Pro Ser Val Phe Tyr
        355                 360                 365
```

```
Gly Asp Tyr Tyr Gly Ile Pro Thr His Ser Val Pro Ala Met Lys Ala
    370                 375                 380

Lys Ile Asp Pro Ile Leu Glu Ala Arg Gln Asn Phe Ala Tyr Gly Thr
385                 390                 395                 400

Gln His Asp Tyr Phe Asp His His Asn Ile Ile Gly Trp Thr Arg Glu
                405                 410                 415

Gly Asn Thr Thr His Pro Asn Ser Gly Leu Ala Thr Ile Met Ser Asp
                420                 425                 430

Gly Pro Gly Gly Glu Lys Trp Met Tyr Val Gly Gln Asn Lys Ala Gly
                435                 440                 445

Gln Val Trp His Asp Ile Thr Gly Asn Lys Pro Gly Thr Val Thr Ile
    450                 455                 460

Asn Ala Asp Gly Trp Ala Asn Phe Ser Val Asn Gly Gly Ser Val Ser
465                 470                 475                 480

Ile Trp Val Lys Arg
                485

<210> SEQ ID NO 2
<211> LENGTH: 485
<212> TYPE: PRT
<213> ORGANISM: Bacillus sp.

<400> SEQUENCE: 2

His His Asn Gly Thr Asn Gly Thr Met Met Gln Tyr Phe Glu Trp Tyr
1               5                   10                  15

Leu Pro Asn Asp Gly Asn His Trp Asn Arg Leu Asn Ser Asp Ala Ser
                20                  25                  30

Asn Leu Lys Ser Lys Gly Ile Thr Ala Val Trp Ile Pro Pro Ala Trp
            35                  40                  45

Lys Gly Ala Ser Gln Asn Asp Val Gly Tyr Gly Ala Tyr Asp Leu Tyr
50                  55                  60

Asp Leu Gly Glu Phe Asn Gln Lys Gly Thr Val Arg Thr Lys Tyr Gly
65                  70                  75                  80

Thr Arg Ser Gln Leu Gln Ala Ala Val Thr Ser Leu Lys Asn Asn Gly
                85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
        115                 120                 125

Gln Glu Val Thr Gly Glu Tyr Thr Ile Glu Ala Trp Thr Arg Phe Asp
    130                 135                 140

Phe Pro Gly Arg Gly Asn Thr His Ser Ser Phe Lys Trp Arg Trp Tyr
145                 150                 155                 160

His Phe Asp Gly Val Asp Trp Asp Gln Ser Arg Arg Leu Asn Asn Arg
                165                 170                 175

Ile Tyr Lys Phe Arg Gly His Gly Lys Ala Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
    210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255
```

```
Thr Gly Lys Asn Met Phe Ala Val Ala Glu Phe Trp Lys Asn Asp Leu
            260                 265                 270

Gly Ala Ile Glu Asn Tyr Leu Gln Lys Thr Asn Trp Asn His Ser Val
            275                 280                 285

Phe Asp Val Pro Leu His Tyr Asn Leu Tyr Asn Ala Ser Lys Ser Gly
            290                 295                 300

Gly Asn Tyr Asp Met Arg Asn Ile Phe Asn Gly Thr Val Val Gln Arg
305                 310                 315                 320

His Pro Ser His Ala Val Thr Phe Val Asp Asn His Asp Ser Gln Pro
                325                 330                 335

Glu Glu Ala Leu Glu Ser Phe Val Glu Glu Trp Phe Lys Pro Leu Ala
            340                 345                 350

Tyr Ala Leu Thr Leu Thr Arg Glu Gln Gly Tyr Pro Ser Val Phe Tyr
            355                 360                 365

Gly Asp Tyr Tyr Gly Ile Pro Thr His Gly Val Pro Ala Met Arg Ser
370                 375                 380

Lys Ile Asp Pro Ile Leu Glu Ala Arg Gln Lys Tyr Ala Tyr Gly Lys
385                 390                 395                 400

Gln Asn Asp Tyr Leu Asp His Ser Asn Ile Ile Gly Trp Thr Arg Glu
            405                 410                 415

Gly Asn Thr Ala His Pro Asn Ser Gly Leu Ala Thr Ile Met Ser Asp
            420                 425                 430

Gly Ala Gly Gly Ser Lys Trp Met Phe Val Gly Arg Asn Lys Ala Gly
            435                 440                 445

Gln Val Trp Ser Asp Ile Thr Gly Asn Arg Thr Gly Thr Val Thr Ile
            450                 455                 460

Asn Ala Asp Gly Trp Gly Asn Phe Ser Val Asn Gly Gly Ser Val Ser
465                 470                 475                 480

Ile Trp Val Asn Lys
            485

<210> SEQ ID NO 3
<211> LENGTH: 485
<212> TYPE: PRT
<213> ORGANISM: Bacillus sp.

<400> SEQUENCE: 3

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Ser Ala Val Trp Ile Pro Pro Ala Trp
            35                  40                  45

Lys Gly Ala Ser Gln Asn Asp Val Gly Tyr Gly Ala Tyr Asp Leu Tyr
50                  55                  60

Asp Leu Gly Glu Phe Asn Gln Lys Gly Thr Ile Arg Thr Lys Tyr Gly
65                  70                  75                  80

Thr Arg Asn Gln Leu Gln Ala Ala Val Asn Ala Leu Lys Ser Asn Gly
            85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
            115                 120                 125

Gln Glu Val Ser Gly Glu Tyr Thr Ile Glu Ala Trp Thr Lys Phe Asp
```

```
            130                 135                 140
Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Lys Leu Asn Asn Arg
                165                 170                 175

Ile Tyr Lys Phe Arg Gly Asp Gly Lys Gly Trp Asp Trp Glu Val Asp
                180                 185                 190

Thr Glu Asn Gly Asn Tyr Asp Tyr Leu Met Tyr Ala Asp Ile Asp Met
                195                 200                 205

Asp His Pro Glu Val Val Asn Glu Leu Arg Asn Trp Gly Val Trp Tyr
            210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255

Thr Gly Lys Asn Met Phe Ala Val Ala Glu Phe Trp Lys Asn Asp Leu
                260                 265                 270

Gly Ala Ile Glu Asn Tyr Leu Asn Lys Thr Asn Trp Asn His Ser Val
            275                 280                 285

Phe Asp Val Pro Leu His Tyr Asn Leu Tyr Asn Ala Ser Lys Ser Gly
290                 295                 300

Gly Asn Tyr Asp Met Arg Gln Ile Phe Asn Gly Thr Val Val Gln Arg
305                 310                 315                 320

His Pro Met His Ala Val Thr Phe Val Asp Asn His Asp Ser Gln Pro
                325                 330                 335

Glu Glu Ala Leu Glu Ser Phe Val Glu Glu Trp Phe Lys Pro Leu Ala
            340                 345                 350

Tyr Ala Leu Thr Leu Thr Arg Glu Gln Gly Tyr Pro Ser Val Phe Tyr
            355                 360                 365

Gly Asp Tyr Tyr Gly Ile Pro Thr His Gly Val Pro Ala Met Lys Ser
            370                 375                 380

Lys Ile Asp Pro Ile Leu Glu Ala Arg Gln Lys Tyr Ala Tyr Gly Arg
385                 390                 395                 400

Gln Asn Asp Tyr Leu Asp His His Asn Ile Ile Gly Trp Thr Arg Glu
                405                 410                 415

Gly Asn Thr Ala His Pro Asn Ser Gly Leu Ala Thr Ile Met Ser Asp
                420                 425                 430

Gly Ala Gly Gly Asn Lys Trp Met Phe Val Gly Arg Asn Lys Ala Gly
            435                 440                 445

Gln Val Trp Thr Asp Ile Thr Gly Asn Arg Ala Gly Thr Val Thr Ile
            450                 455                 460

Asn Ala Asp Gly Trp Gly Asn Phe Ser Val Asn Gly Gly Ser Val Ser
465                 470                 475                 480

Ile Trp Val Asn Lys
                485

<210> SEQ ID NO 4
<211> LENGTH: 485
<212> TYPE: PRT
<213> ORGANISM: Bacillus sp.

<400> SEQUENCE: 4

His His Asn Gly Thr Asn Gly Thr Met Met Gln Tyr Phe Glu Trp Tyr
1               5                   10                  15
```

-continued

```
Leu Pro Asn Asp Gly Asn His Trp Asn Arg Leu Arg Asp Ala Ala
             20                  25                  30

Asn Leu Lys Ser Lys Gly Ile Thr Ala Val Trp Ile Pro Pro Ala Trp
         35                  40                  45

Lys Gly Thr Ser Gln Asn Asp Val Gly Tyr Gly Ala Tyr Asp Leu Tyr
     50                  55                  60

Asp Leu Gly Glu Phe Asn Gln Lys Gly Thr Val Arg Thr Lys Tyr Gly
 65                  70                  75                  80

Thr Arg Asn Gln Leu Gln Ala Ala Val Thr Ser Leu Lys Asn Asn Gly
                 85                  90                  95

Ile Gln Val Tyr Gly Asp Val Val Met Asn His Lys Gly Gly Ala Asp
             100                 105                 110

Gly Thr Glu Ile Val Asn Ala Val Glu Val Asn Arg Ser Asn Arg Asn
         115                 120                 125

Gln Glu Thr Ser Gly Glu Tyr Ala Ile Glu Ala Trp Thr Lys Phe Asp
     130                 135                 140

Phe Pro Gly Arg Gly Asn Asn His Ser Ser Phe Lys Trp Arg Trp Tyr
145                 150                 155                 160

His Phe Asp Gly Thr Asp Trp Asp Gln Ser Arg Gln Leu Gln Asn Lys
                 165                 170                 175

Ile Tyr Lys Phe Arg Gly Thr Gly Lys Ala Trp Asp Trp Glu Val Asp
             180                 185                 190

Thr Glu Asn Gly Asn Tyr Asp Tyr Leu Met Tyr Ala Asp Val Asp Met
         195                 200                 205

Asp His Pro Glu Val Ile His Glu Leu Arg Asn Trp Gly Val Trp Tyr
     210                 215                 220

Thr Asn Thr Leu Asn Leu Asp Gly Phe Arg Ile Asp Ala Val Lys His
225                 230                 235                 240

Ile Lys Tyr Ser Phe Thr Arg Asp Trp Leu Thr His Val Arg Asn Thr
                 245                 250                 255

Thr Gly Lys Pro Met Phe Ala Val Ala Glu Phe Trp Lys Asn Asp Leu
             260                 265                 270

Gly Ala Ile Glu Asn Tyr Leu Asn Lys Thr Ser Trp Asn His Ser Val
         275                 280                 285

Phe Asp Val Pro Leu His Tyr Asn Leu Tyr Asn Ala Ser Asn Ser Gly
     290                 295                 300

Gly Tyr Tyr Asp Met Arg Asn Ile Leu Asn Gly Ser Val Val Gln Lys
305                 310                 315                 320

His Pro Thr His Ala Val Thr Phe Val Asp Asn His Asp Ser Gln Pro
                 325                 330                 335

Gly Glu Ala Leu Glu Ser Phe Val Gln Gln Trp Phe Lys Pro Leu Ala
             340                 345                 350

Tyr Ala Leu Val Leu Thr Arg Glu Gln Gly Tyr Pro Ser Val Phe Tyr
         355                 360                 365

Gly Asp Tyr Tyr Gly Ile Pro Thr His Gly Val Pro Ala Met Lys Ser
     370                 375                 380

Lys Ile Asp Pro Leu Leu Gln Ala Arg Gln Thr Phe Ala Tyr Gly Thr
385                 390                 395                 400

Gln His Asp Tyr Phe Asp His Asp Ile Ile Gly Trp Thr Arg Glu
                 405                 410                 415

Gly Asn Ser Ser His Pro Asn Ser Gly Leu Ala Thr Ile Met Ser Asp
             420                 425                 430

Gly Pro Gly Gly Asn Lys Trp Met Tyr Val Gly Lys Asn Lys Ala Gly
```

```
                  435                 440                 445
Gln Val Trp Arg Asp Ile Thr Gly Asn Arg Thr Gly Thr Val Thr Ile
        450                 455                 460

Asn Ala Asp Gly Trp Gly Asn Phe Ser Val Asn Gly Gly Ser Val Ser
465                 470                 475                 480

Val Trp Val Lys Gln
                485

<210> SEQ ID NO 5
<211> LENGTH: 485
<212> TYPE: PRT
<213> ORGANISM: Bacillus sp.

<400> SEQUENCE: 5

His His Asn Gly Thr Asn Gly Thr Met Met Gln Tyr Phe Glu Trp His
1               5                  10                  15

Leu Pro Asn Asp Gly Asn His Trp Asn Arg Leu Arg Asp Asp Ala Ala
                20                  25                  30

Asn Leu Lys Ser Lys Gly Ile Thr Ala Val Trp Ile Pro Pro Ala Trp
            35                  40                  45

Lys Gly Thr Ser Gln Asn Asp Val Gly Tyr Gly Ala Tyr Asp Leu Tyr
        50                  55                  60

Asp Leu Gly Glu Phe Asn Gln Lys Gly Thr Val Arg Thr Lys Tyr Gly
65                  70                  75                  80

Thr Arg Ser Gln Leu Gln Gly Ala Val Thr Ser Leu Lys Asn Asn Gly
                85                  90                  95

Ile Gln Val Tyr Gly Asp Val Val Met Asn His Lys Gly Gly Ala Asp
            100                 105                 110

Gly Thr Glu Met Val Asn Ala Val Glu Val Asn Arg Ser Asn Arg Asn
        115                 120                 125

Gln Glu Ile Ser Gly Glu Tyr Thr Ile Glu Ala Trp Thr Lys Phe Asp
130                 135                 140

Phe Pro Gly Arg Gly Asn Thr His Ser Asn Phe Lys Trp Arg Trp Tyr
145                 150                 155                 160

His Phe Asp Gly Thr Asp Trp Asp Gln Ser Arg Gln Leu Gln Asn Lys
                165                 170                 175

Ile Tyr Lys Phe Arg Gly Thr Gly Lys Ala Trp Asp Trp Glu Val Asp
            180                 185                 190

Ile Glu Asn Gly Asn Tyr Asp Tyr Leu Met Tyr Ala Asp Ile Asp Met
        195                 200                 205

Asp His Pro Glu Val Ile Asn Glu Leu Arg Asn Trp Gly Val Trp Tyr
210                 215                 220

Thr Asn Thr Leu Asn Leu Asp Gly Phe Arg Ile Asp Ala Val Lys His
225                 230                 235                 240

Ile Lys Tyr Ser Tyr Thr Arg Asp Trp Leu Thr His Val Arg Asn Thr
                245                 250                 255

Thr Gly Lys Pro Met Phe Ala Val Ala Glu Phe Trp Lys Asn Asp Leu
            260                 265                 270

Ala Ala Ile Glu Asn Tyr Leu Asn Lys Thr Ser Trp Asn His Ser Val
        275                 280                 285

Phe Asp Val Pro Leu His Tyr Asn Leu Tyr Asn Ala Ser Asn Ser Gly
290                 295                 300

Gly Tyr Phe Asp Met Arg Asn Ile Leu Asn Gly Ser Val Val Gln Lys
305                 310                 315                 320
```

```
His Pro Ile His Ala Val Thr Phe Val Asp Asn His Asp Ser Gln Pro
                325                 330                 335

Gly Glu Ala Leu Glu Ser Phe Val Gln Ser Trp Phe Lys Pro Leu Ala
            340                 345                 350

Tyr Ala Leu Ile Leu Thr Arg Glu Gln Gly Tyr Pro Ser Val Phe Tyr
        355                 360                 365

Gly Asp Tyr Tyr Gly Ile Pro Thr His Gly Val Pro Ser Met Lys Ser
    370                 375                 380

Lys Ile Asp Pro Leu Leu Gln Ala Arg Gln Thr Tyr Ala Tyr Gly Thr
385                 390                 395                 400

Gln His Asp Tyr Phe Asp His His Asp Ile Ile Gly Trp Thr Arg Glu
                405                 410                 415

Gly Asp Ser Ser His Pro Asn Ser Gly Leu Ala Thr Ile Met Ser Asp
            420                 425                 430

Gly Pro Gly Gly Asn Lys Trp Met Tyr Val Gly Lys His Lys Ala Gly
        435                 440                 445

Gln Val Trp Arg Asp Ile Thr Gly Asn Arg Ser Gly Thr Val Thr Ile
    450                 455                 460

Asn Ala Asp Gly Trp Gly Asn Phe Thr Val Asn Gly Gly Ala Val Ser
465                 470                 475                 480

Val Trp Val Lys Gln
                485

<210> SEQ ID NO 6
<211> LENGTH: 485
<212> TYPE: PRT
<213> ORGANISM: Bacillus sp.

<400> SEQUENCE: 6

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
                20                  25                  30

Asn Leu Lys Asp Lys Gly Ile Thr Ala Val Trp Ile Pro Pro Ala Trp
            35                  40                  45

Lys Gly Ala Ser Gln Asn Asp Val Gly Tyr Gly Ala Tyr Asp Leu Tyr
        50                  55                  60

Asp Leu Gly Glu Phe Asn Gln Lys Gly Thr Val Arg Thr Lys Tyr Gly
65                  70                  75                  80

Thr Arg Asn Gln Leu Gln Ala Ala Val Thr Ala Leu Lys Ser Asn Gly
                85                  90                  95

Ile Gln Val Tyr Gly Asp Val Val Met Asn His Lys Gly Gly Ala Asp
            100                 105                 110

Ala Thr Glu Trp Val Arg Ala Val Glu Val Asn Pro Ser Asn Arg Asn
        115                 120                 125

Gln Glu Val Ser Gly Asp Tyr Thr Ile Glu Ala Trp Thr Lys Phe Asp
    130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Gln Leu Gln Asn Arg
                165                 170                 175

Ile Tyr Lys Phe Arg Gly Asp Gly Lys Gly Trp Asp Trp Glu Val Asp
            180                 185                 190

Thr Glu Asn Gly Asn Tyr Asp Tyr Leu Met Tyr Ala Asp Ile Asp Met
        195                 200                 205
```

Asp His Pro Glu Val Val Asn Glu Leu Arg Asn Trp Gly Val Trp Tyr
    210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Leu Thr His Val Arg Asn Thr
                245                 250                 255

Thr Gly Lys Asn Met Phe Ala Val Ala Glu Phe Trp Lys Asn Asp Ile
            260                 265                 270

Gly Ala Ile Glu Asn Tyr Leu Ser Lys Thr Asn Trp Asn His Ser Val
        275                 280                 285

Phe Asp Val Pro Leu His Tyr Asn Leu Tyr Asn Ala Ser Arg Ser Gly
    290                 295                 300

Gly Asn Tyr Asp Met Arg Gln Ile Phe Asn Gly Thr Val Val Gln Arg
305                 310                 315                 320

His Pro Thr His Ala Val Thr Phe Val Asp Asn His Asp Ser Gln Pro
                325                 330                 335

Glu Glu Ala Leu Glu Ser Phe Val Glu Glu Trp Phe Lys Pro Leu Ala
            340                 345                 350

Tyr Ala Leu Thr Leu Thr Arg Asp Gln Gly Tyr Pro Ser Val Phe Tyr
        355                 360                 365

Gly Asp Tyr Tyr Gly Ile Pro Thr His Gly Val Pro Ala Met Lys Ser
370                 375                 380

Lys Ile Asp Pro Ile Leu Glu Ala Arg Gln Lys Tyr Ala Tyr Gly Lys
385                 390                 395                 400

Gln Asn Asp Tyr Leu Asp His His Asn Met Ile Gly Trp Thr Arg Glu
                405                 410                 415

Gly Asn Thr Ala His Pro Asn Ser Gly Leu Ala Thr Ile Met Ser Asp
            420                 425                 430

Gly Pro Gly Gly Asn Lys Trp Met Tyr Val Gly Arg Asn Lys Ala Gly
        435                 440                 445

Gln Val Trp Arg Asp Ile Thr Gly Asn Arg Ser Gly Thr Val Thr Ile
    450                 455                 460

Asn Ala Asp Gly Trp Gly Asn Phe Ser Val Asn Gly Gly Ser Val Ser
465                 470                 475                 480

Ile Trp Val Asn Asn
            485

<210> SEQ ID NO 7
<211> LENGTH: 483
<212> TYPE: PRT
<213> ORGANISM: Artificial
<220> FEATURE:
<223> OTHER INFORMATION: Variant of SEQ ID NO:1

<400> SEQUENCE: 7

His His Asn Gly Thr Asn Gly Thr Met Met Gln Tyr Phe Glu Trp His
1               5                   10                  15

Leu Pro Asn Asp Gly Asn His Trp Asn Arg Leu Arg Asp Asp Ala Ser
            20                  25                  30

Asn Leu Arg Asn Arg Gly Ile Thr Ala Ile Trp Ile Pro Pro Ala Trp
        35                  40                  45

Lys Gly Thr Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

```
Thr Arg Ser Gln Leu Glu Ser Ala Ile His Ala Leu Lys Asn Asn Gly
                85                  90                  95

Val Gln Val Tyr Gly Asp Val Val Met Asn His Lys Gly Gly Ala Asp
            100                 105                 110

Ala Thr Glu Asn Val Leu Ala Val Glu Val Asn Pro Asn Asn Arg Asn
        115                 120                 125

Gln Glu Ile Ser Gly Asp Tyr Thr Ile Glu Ala Trp Thr Lys Phe Asp
    130                 135                 140

Phe Pro Gly Arg Gly Asn Thr Tyr Ser Asp Phe Lys Trp Arg Trp Tyr
145                 150                 155                 160

His Phe Asp Gly Val Asp Trp Asp Gln Ser Arg Gln Phe Gln Asn Arg
                165                 170                 175

Ile Tyr Lys Phe Arg Gly Lys Ala Trp Asp Trp Glu Val Asp Ser Glu
            180                 185                 190

Asn Gly Asn Tyr Asp Tyr Leu Met Tyr Ala Asp Val Asp Met Asp His
        195                 200                 205

Pro Glu Val Val Asn Glu Leu Arg Arg Trp Gly Glu Trp Tyr Thr Asn
    210                 215                 220

Thr Leu Asn Leu Asp Gly Phe Arg Ile Asp Ala Val Lys His Ile Lys
225                 230                 235                 240

Tyr Ser Phe Thr Arg Asp Trp Leu Thr His Val Arg Asn Ala Thr Gly
                245                 250                 255

Lys Glu Met Phe Ala Val Ala Glu Phe Trp Lys Asn Asp Leu Gly Ala
            260                 265                 270

Leu Glu Asn Tyr Leu Asn Lys Thr Asn Trp Asn His Ser Val Phe Asp
        275                 280                 285

Val Pro Leu His Tyr Asn Leu Tyr Asn Ala Ser Asn Ser Gly Gly Asn
    290                 295                 300

Tyr Asp Met Ala Lys Leu Leu Asn Gly Thr Val Val Gln Lys His Pro
305                 310                 315                 320

Met His Ala Val Thr Phe Val Asp Asn His Asp Ser Gln Pro Gly Glu
                325                 330                 335

Ser Leu Glu Ser Phe Val Gln Glu Trp Phe Lys Pro Leu Ala Tyr Ala
            340                 345                 350

Leu Ile Leu Thr Arg Glu Gln Gly Tyr Pro Ser Val Phe Tyr Gly Asp
        355                 360                 365

Tyr Tyr Gly Ile Pro Thr His Ser Val Pro Ala Met Lys Ala Lys Ile
370                 375                 380

Asp Pro Ile Leu Glu Ala Arg Gln Asn Phe Ala Tyr Gly Thr Gln His
385                 390                 395                 400

Asp Tyr Phe Asp His His Asn Ile Ile Gly Trp Thr Arg Glu Gly Asn
                405                 410                 415

Thr Thr His Pro Asn Ser Gly Leu Ala Thr Ile Met Ser Asp Gly Pro
            420                 425                 430

Gly Gly Glu Lys Trp Met Tyr Val Gly Gln Asn Lys Ala Gly Gln Val
        435                 440                 445

Trp His Asp Ile Thr Gly Asn Lys Pro Gly Thr Val Thr Ile Asn Ala
    450                 455                 460

Asp Gly Trp Ala Asn Phe Ser Val Asn Gly Gly Ser Val Ser Ile Trp
465                 470                 475                 480

Val Lys Arg
```

```
<210> SEQ ID NO 8
<211> LENGTH: 483
<212> TYPE: PRT
<213> ORGANISM: Artificial
<220> FEATURE:
<223> OTHER INFORMATION: Variant of SEQ ID NO:2

<400> SEQUENCE: 8

His His Asn Gly Thr Asn Gly Thr Met Met Gln Tyr Phe Glu Trp Tyr
1               5                   10                  15

Leu Pro Asn Asp Gly Asn His Trp Asn Arg Leu Asn Ser Asp Ala Ser
            20                  25                  30

Asn Leu Lys Ser Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Ser Gln Leu Gln Ala Ala Val Thr Ser Leu Lys Asn Asn Gly
                85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
        115                 120                 125

Gln Glu Val Thr Gly Glu Tyr Thr Ile Glu Ala Trp Thr Arg Phe Asp
    130                 135                 140

Phe Pro Gly Arg Gly Asn Thr His Ser Ser Phe Lys Trp Arg Trp Tyr
145                 150                 155                 160

His Phe Asp Gly Val Asp Trp Asp Gln Ser Arg Arg Leu Asn Asn Arg
                165                 170                 175

Ile Tyr Lys Phe Arg Gly Lys Ala Trp Asp Trp Glu Val Asp Thr Glu
            180                 185                 190

Asn Gly Asn Tyr Asp Tyr Leu Met Tyr Ala Asp Ile Asp Met Asp His
        195                 200                 205

Pro Glu Val Val Asn Glu Leu Arg Asn Trp Gly Val Trp Tyr Thr Asn
    210                 215                 220

Thr Leu Gly Leu Asp Gly Phe Arg Ile Asp Ala Val Lys His Ile Lys
225                 230                 235                 240

Tyr Ser Phe Thr Arg Asp Trp Ile Asn His Val Arg Ser Ala Thr Gly
                245                 250                 255

Lys Asn Met Phe Ala Val Ala Glu Phe Trp Lys Asn Asp Leu Gly Ala
            260                 265                 270

Ile Glu Asn Tyr Leu Gln Lys Thr Asn Trp Asn His Ser Val Phe Asp
        275                 280                 285

Val Pro Leu His Tyr Asn Leu Tyr Asn Ala Ser Lys Ser Gly Gly Asn
    290                 295                 300

Tyr Asp Met Arg Asn Ile Phe Asn Gly Thr Val Val Gln Arg His Pro
305                 310                 315                 320

Ser His Ala Val Thr Phe Val Asp Asn His Asp Ser Gln Pro Glu Glu
                325                 330                 335

Ala Leu Glu Ser Phe Val Glu Glu Trp Phe Lys Pro Leu Ala Tyr Ala
            340                 345                 350

Leu Thr Leu Thr Arg Glu Gln Gly Tyr Pro Ser Val Phe Tyr Gly Asp
        355                 360                 365

Tyr Tyr Gly Ile Pro Thr His Gly Val Pro Ala Met Arg Ser Lys Ile
```

```
                370                 375                 380
Asp Pro Ile Leu Glu Ala Arg Gln Lys Tyr Ala Tyr Gly Lys Gln Asn
385                 390                 395                 400

Asp Tyr Leu Asp His His Asn Ile Ile Gly Trp Thr Arg Glu Gly Asn
                405                 410                 415

Thr Ala His Pro Asn Ser Gly Leu Ala Thr Ile Met Ser Asp Gly Ala
                420                 425                 430

Gly Gly Ser Lys Trp Met Phe Val Gly Arg Asn Lys Ala Gly Gln Val
                435                 440                 445

Trp Ser Asp Ile Thr Gly Asn Arg Thr Gly Thr Val Thr Ile Asn Ala
450                 455                 460

Asp Gly Trp Gly Asn Phe Ser Val Asn Gly Ser Val Ser Ile Trp
465                 470                 475                 480

Val Asn Lys

<210> SEQ ID NO 9
<211> LENGTH: 483
<212> TYPE: PRT
<213> ORGANISM: Artificial
<220> FEATURE:
<223> OTHER INFORMATION: Variant of SEQ ID NO:3

<400> SEQUENCE: 9

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
                20                  25                  30

Asn Leu Lys Asp Lys Gly Ile Ser Ala Val Trp Ile Pro Pro Ala Trp
                35                  40                  45

Lys Gly Ala Ser Gln Asn Asp Val Gly Tyr Gly Ala Tyr Asp Leu Tyr
50                  55                  60

Asp Leu Gly Glu Phe Asn Gln Lys Gly Thr Ile Arg Thr Lys Tyr Gly
65              70                  75                  80

Thr Arg Asn Gln Leu Gln Ala Ala Val Asn Ala Leu Lys Ser Asn Gly
                85                  90                  95

Ile Gln Val Tyr Gly Asp Val Val Met Asn His Lys Gly Gly Ala Asp
                100                 105                 110

Ala Thr Glu Met Val Arg Ala Val Glu Val Asn Pro Asn Asn Arg Asn
                115                 120                 125

Gln Glu Val Ser Gly Glu Tyr Thr Ile Glu Ala Trp Thr Lys Phe Asp
130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Lys Leu Asn Asn Arg
                165                 170                 175

Ile Tyr Lys Phe Arg Gly Lys Gly Trp Asp Trp Glu Val Asp Thr Glu
                180                 185                 190

Asn Gly Asn Tyr Asp Tyr Leu Met Tyr Ala Asp Ile Asp Met Asp His
                195                 200                 205

Pro Glu Val Val Asn Glu Leu Arg Asn Trp Gly Val Trp Tyr Thr Asn
                210                 215                 220

Thr Leu Gly Leu Asp Gly Phe Arg Ile Asp Ala Val Lys His Ile Lys
225                 230                 235                 240

Tyr Ser Phe Thr Arg Asp Trp Ile Asn His Val Arg Ser Ala Thr Gly
                245                 250                 255
```

-continued

```
Lys Asn Met Phe Ala Val Ala Glu Phe Trp Lys Asn Asp Leu Gly Ala
            260                 265                 270
Ile Glu Asn Tyr Leu Asn Lys Thr Asn Trp Asn His Ser Val Phe Asp
        275                 280                 285
Val Pro Leu His Tyr Asn Leu Tyr Asn Ala Ser Lys Ser Gly Gly Asn
    290                 295                 300
Tyr Asp Met Arg Gln Ile Phe Asn Gly Thr Val Val Gln Arg His Pro
305                 310                 315                 320
Met His Ala Val Thr Phe Val Asp Asn His Asp Ser Gln Pro Glu Glu
                325                 330                 335
Ala Leu Glu Ser Phe Val Glu Glu Trp Phe Lys Pro Leu Ala Tyr Ala
            340                 345                 350
Leu Thr Leu Thr Arg Glu Gln Gly Tyr Pro Ser Val Phe Tyr Gly Asp
        355                 360                 365
Tyr Tyr Gly Ile Pro Thr His Gly Val Pro Ala Met Lys Ser Lys Ile
    370                 375                 380
Asp Pro Ile Leu Glu Ala Arg Gln Lys Tyr Ala Tyr Gly Arg Gln Asn
385                 390                 395                 400
Asp Tyr Leu Asp His His Asn Ile Ile Gly Trp Thr Arg Glu Gly Asn
                405                 410                 415
Thr Ala His Pro Asn Ser Gly Leu Ala Thr Ile Met Ser Asp Gly Ala
            420                 425                 430
Gly Gly Asn Lys Trp Met Phe Val Gly Arg Asn Lys Ala Gly Gln Val
        435                 440                 445
Trp Thr Asp Ile Thr Gly Asn Arg Ala Gly Thr Val Thr Ile Asn Ala
    450                 455                 460
Asp Gly Trp Gly Asn Phe Ser Val Asn Gly Gly Ser Val Ser Ile Trp
465                 470                 475                 480
Val Asn Lys

<210> SEQ ID NO 10
<211> LENGTH: 483
<212> TYPE: PRT
<213> ORGANISM: Artificial
<220> FEATURE:
<223> OTHER INFORMATION: Variant of SEQ ID NO:4

<400> SEQUENCE: 10

His His Asn Gly Thr Asn Gly Thr Met Met Gln Tyr Phe Glu Trp Tyr
1               5                   10                  15
Leu Pro Asn Asp Gly Asn His Trp Asn Arg Leu Arg Asp Asp Ala Ala
            20                  25                  30
Asn Leu Lys Ser Lys Gly Ile Thr Ala Val Trp Ile Pro Pro Ala Trp
        35                  40                  45
Lys Gly Thr Ser Gln Asn Asp Val Gly Tyr Gly Ala Tyr Asp Leu Tyr
    50                  55                  60
Asp Leu Gly Glu Phe Asn Gln Lys Gly Thr Val Arg Thr Lys Tyr Gly
65                  70                  75                  80
Thr Arg Asn Gln Leu Gln Ala Ala Val Thr Ser Leu Lys Asn Asn Gly
                85                  90                  95
Ile Gln Val Tyr Gly Asp Val Val Met Asn His Lys Gly Gly Ala Asp
            100                 105                 110
Gly Thr Glu Ile Val Asn Ala Val Glu Val Asn Arg Ser Asn Arg Asn
        115                 120                 125
```

```
Gln Glu Thr Ser Gly Glu Tyr Ala Ile Glu Ala Trp Thr Lys Phe Asp
    130                 135                 140

Phe Pro Gly Arg Gly Asn Asn His Ser Ser Phe Lys Trp Arg Trp Tyr
145                 150                 155                 160

His Phe Asp Gly Thr Asp Trp Asp Gln Ser Arg Gln Leu Gln Asn Lys
                165                 170                 175

Ile Tyr Lys Phe Arg Gly Lys Ala Trp Asp Trp Glu Val Asp Thr Glu
            180                 185                 190

Asn Gly Asn Tyr Asp Tyr Leu Met Tyr Ala Asp Val Asp Met Asp His
        195                 200                 205

Pro Glu Val Ile His Glu Leu Arg Asn Trp Gly Val Trp Tyr Thr Asn
210                 215                 220

Thr Leu Asn Leu Asp Gly Phe Arg Ile Asp Ala Val Lys His Ile Lys
225                 230                 235                 240

Tyr Ser Phe Thr Arg Asp Trp Leu Thr His Val Arg Asn Thr Thr Gly
                245                 250                 255

Lys Pro Met Phe Ala Val Ala Glu Phe Trp Lys Asn Asp Leu Gly Ala
            260                 265                 270

Ile Glu Asn Tyr Leu Asn Lys Thr Ser Trp Asn His Ser Val Phe Asp
        275                 280                 285

Val Pro Leu His Tyr Asn Leu Tyr Asn Ala Ser Asn Ser Gly Gly Tyr
290                 295                 300

Tyr Asp Met Arg Asn Ile Leu Asn Gly Ser Val Val Gln Lys His Pro
305                 310                 315                 320

Thr His Ala Val Thr Phe Val Asp Asn His Asp Ser Gln Pro Gly Glu
                325                 330                 335

Ala Leu Glu Ser Phe Val Gln Gln Trp Phe Lys Pro Leu Ala Tyr Ala
            340                 345                 350

Leu Val Leu Thr Arg Glu Gln Gly Tyr Pro Ser Val Phe Tyr Gly Asp
        355                 360                 365

Tyr Tyr Gly Ile Pro Thr His Gly Val Pro Ala Met Lys Ser Lys Ile
370                 375                 380

Asp Pro Leu Leu Gln Ala Arg Gln Thr Phe Ala Tyr Gly Thr Gln His
385                 390                 395                 400

Asp Tyr Phe Asp His His Asp Ile Ile Gly Trp Thr Arg Glu Gly Asn
                405                 410                 415

Ser Ser His Pro Asn Ser Gly Leu Ala Thr Ile Met Ser Asp Gly Pro
            420                 425                 430

Gly Gly Asn Lys Trp Met Tyr Val Gly Lys Asn Lys Ala Gly Gln Val
        435                 440                 445

Trp Arg Asp Ile Thr Gly Asn Arg Thr Gly Thr Val Thr Ile Asn Ala
450                 455                 460

Asp Gly Trp Gly Asn Phe Ser Val Asn Gly Gly Ser Val Ser Val Trp
465                 470                 475                 480

Val Lys Gln

<210> SEQ ID NO 11
<211> LENGTH: 483
<212> TYPE: PRT
<213> ORGANISM: Artificial
<220> FEATURE:
<223> OTHER INFORMATION: Variant of SEQ ID NO:5

<400> SEQUENCE: 11

His His Asn Gly Thr Asn Gly Thr Met Met Gln Tyr Phe Glu Trp His
```

```
1               5                    10                   15
Leu Pro Asn Asp Gly Asn His Trp Asn Arg Leu Arg Asp Ala Ala
                20                  25                  30
Asn Leu Lys Ser Lys Gly Ile Thr Ala Val Trp Ile Pro Pro Ala Trp
                35                  40                  45
Lys Gly Thr Ser Gln Asn Asp Val Gly Tyr Gly Ala Tyr Asp Leu Tyr
        50                  55                  60
Asp Leu Gly Glu Phe Asn Gln Lys Gly Thr Val Arg Thr Lys Tyr Gly
65                  70                  75                  80
Thr Arg Ser Gln Leu Gln Gly Ala Val Thr Ser Leu Lys Asn Asn Gly
                85                  90                  95
Ile Gln Val Tyr Gly Asp Val Val Met Asn His Lys Gly Gly Ala Asp
                100                 105                 110
Gly Thr Glu Met Val Asn Ala Val Glu Val Asn Arg Ser Asn Arg Asn
                115                 120                 125
Gln Glu Ile Ser Gly Glu Tyr Thr Ile Glu Ala Trp Thr Lys Phe Asp
                130                 135                 140
Phe Pro Gly Arg Gly Asn Thr His Ser Asn Phe Lys Trp Arg Trp Tyr
145                 150                 155                 160
His Phe Asp Gly Thr Asp Trp Asp Gln Ser Arg Gln Leu Gln Asn Lys
                165                 170                 175
Ile Tyr Lys Phe Arg Gly Lys Ala Trp Asp Trp Glu Val Asp Ile Glu
                180                 185                 190
Asn Gly Asn Tyr Asp Tyr Leu Met Tyr Ala Asp Ile Asp Met Asp His
                195                 200                 205
Pro Glu Val Ile Asn Glu Leu Arg Asn Trp Gly Val Trp Tyr Thr Asn
210                 215                 220
Thr Leu Asn Leu Asp Gly Phe Arg Ile Asp Ala Val Lys His Ile Lys
225                 230                 235                 240
Tyr Ser Tyr Thr Arg Asp Trp Leu Thr His Val Arg Asn Thr Thr Gly
                245                 250                 255
Lys Pro Met Phe Ala Val Ala Glu Phe Trp Lys Asn Asp Leu Ala Ala
                260                 265                 270
Ile Glu Asn Tyr Leu Asn Lys Thr Ser Trp Asn His Ser Val Phe Asp
                275                 280                 285
Val Pro Leu His Tyr Asn Leu Tyr Asn Ala Ser Asn Ser Gly Gly Tyr
                290                 295                 300
Phe Asp Met Arg Asn Ile Leu Asn Gly Ser Val Val Gln Lys His Pro
305                 310                 315                 320
Ile His Ala Val Thr Phe Val Asp Asn His Asp Ser Gln Pro Gly Glu
                325                 330                 335
Ala Leu Glu Ser Phe Val Gln Ser Trp Phe Lys Pro Leu Ala Tyr Ala
                340                 345                 350
Leu Ile Leu Thr Arg Glu Gln Gly Tyr Pro Ser Val Phe Tyr Gly Asp
                355                 360                 365
Tyr Tyr Gly Ile Pro Thr His Gly Val Pro Ser Met Lys Ser Lys Ile
        370                 375                 380
Asp Pro Leu Leu Gln Ala Arg Gln Thr Tyr Ala Tyr Gly Thr Gln His
385                 390                 395                 400
Asp Tyr Phe Asp His His Asp Ile Ile Gly Trp Thr Arg Glu Gly Asp
                405                 410                 415
Ser Ser His Pro Asn Ser Gly Leu Ala Thr Ile Met Ser Asp Gly Pro
                420                 425                 430
```

```
Gly Gly Asn Lys Trp Met Tyr Val Gly Lys His Lys Ala Gly Gln Val
            435                 440                 445

Trp Arg Asp Ile Thr Gly Asn Arg Ser Gly Thr Val Thr Ile Asn Ala
450                 455                 460

Asp Gly Trp Gly Asn Phe Thr Val Asn Gly Gly Ala Val Ser Val Trp
465                 470                 475                 480

Val Lys Gln

<210> SEQ ID NO 12
<211> LENGTH: 483
<212> TYPE: PRT
<213> ORGANISM: Artificial
<220> FEATURE:
<223> OTHER INFORMATION: Variant of SEQ ID NO:6

<400> SEQUENCE: 12

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
                20                  25                  30

Asn Leu Lys Asp Lys Gly Ile Thr Ala Val Trp Ile Pro Pro Ala Trp
            35                  40                  45

Lys Gly Ala Ser Gln Asn Asp Val Gly Tyr Gly Ala Tyr Asp Leu Tyr
50                  55                  60

Asp Leu Gly Glu Phe Asn Gln Lys Gly Thr Val Arg Thr Lys Tyr Gly
65                  70                  75                  80

Thr Arg Asn Gln Leu Gln Ala Ala Val Thr Ala Leu Lys Ser Asn Gly
                85                  90                  95

Ile Gln Val Tyr Gly Asp Val Val Met Asn His Lys Gly Gly Ala Asp
            100                 105                 110

Ala Thr Glu Trp Val Arg Ala Val Glu Val Asn Pro Ser Asn Arg Asn
        115                 120                 125

Gln Glu Val Ser Gly Asp Tyr Thr Ile Glu Ala Trp Thr Lys Phe Asp
130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Gln Leu Gln Asn Arg
                165                 170                 175

Ile Tyr Lys Phe Arg Gly Lys Gly Trp Asp Trp Glu Val Asp Thr Glu
            180                 185                 190

Asn Gly Asn Tyr Asp Tyr Leu Met Tyr Ala Asp Ile Asp Met Asp His
        195                 200                 205

Pro Glu Val Val Asn Glu Leu Arg Asn Trp Gly Val Trp Tyr Thr Asn
210                 215                 220

Thr Leu Gly Leu Asp Gly Phe Arg Ile Asp Ala Val Lys His Ile Lys
225                 230                 235                 240

Tyr Ser Phe Thr Arg Asp Trp Leu Thr His Val Arg Asn Thr Thr Gly
                245                 250                 255

Lys Asn Met Phe Ala Val Ala Glu Phe Trp Lys Asn Asp Ile Gly Ala
            260                 265                 270

Ile Glu Asn Tyr Leu Ser Lys Thr Asn Trp Asn His Ser Val Phe Asp
        275                 280                 285

Val Pro Leu His Tyr Asn Leu Tyr Asn Ala Ser Arg Ser Gly Gly Asn
290                 295                 300
```

```
                                        -continued

Tyr Asp Met Arg Gln Ile Phe Asn Gly Thr Val Val Gln Arg His Pro
305                 310                 315                 320

Thr His Ala Val Thr Phe Val Asp Asn His Asp Ser Gln Pro Glu Glu
                325                 330                 335

Ala Leu Glu Ser Phe Val Glu Glu Trp Phe Lys Pro Leu Ala Tyr Ala
                340                 345                 350

Leu Thr Leu Thr Arg Asp Gln Gly Tyr Pro Ser Val Phe Tyr Gly Asp
        355                 360                 365

Tyr Tyr Gly Ile Pro Thr His Gly Val Pro Ala Met Lys Ser Lys Ile
    370                 375                 380

Asp Pro Ile Leu Glu Ala Arg Gln Lys Tyr Ala Tyr Gly Lys Gln Asn
385                 390                 395                 400

Asp Tyr Leu Asp His His Asn Met Ile Gly Trp Thr Arg Glu Gly Asn
                405                 410                 415

Thr Ala His Pro Asn Ser Gly Leu Ala Thr Ile Met Ser Asp Gly Pro
                420                 425                 430

Gly Gly Asn Lys Trp Met Tyr Val Gly Arg Asn Lys Ala Gly Gln Val
            435                 440                 445

Trp Arg Asp Ile Thr Gly Asn Arg Ser Gly Thr Val Thr Ile Asn Ala
        450                 455                 460

Asp Gly Trp Gly Asn Phe Ser Val Asn Gly Gly Ser Val Ser Ile Trp
465                 470                 475                 480

Val Asn Asn
```